United States Patent
Brant et al.

(10) Patent No.: US 6,392,025 B1
(45) Date of Patent: May 21, 2002

(54) HUMAN NHE3 PROTEIN AND NON-HUMAN CELLS EXPRESSING SAME

(75) Inventors: Steven R. Brant, Baltimore; C. H. Chris Yun, Timonium; Mark Donowitz, Baltimore, all of MD (US)

(73) Assignee: Tranzmembrane, LLC, Reistertown, MD (US)

( * ) Notice: Subject to any disclaimer, the term of this patent is extended or adjusted under 35 U.S.C. 154(b) by 0 days.

(21) Appl. No.: 09/097,053

(22) Filed: Jun. 15, 1998

Related U.S. Application Data

(62) Division of application No. 08/677,734, filed on Jul. 10, 1996, now Pat. No. 5,871,919.
(60) Provisional application No. 60/001,061, filed on Jul. 11, 1995.

(51) Int. Cl.[7] ........................ C07H 21/04; C12Q 1/68; C12P 21/06; C12N 5/06; C07K 14/435
(52) U.S. Cl. .................... 536/23.5; 536/23.1; 435/6; 435/7.1; 435/69.1; 435/325; 530/350
(58) Field of Search ..................... 530/350; 536/23.1, 536/23.5, 607.1; 435/69.1, 325

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 5,359,045 A | 10/1994 | Soubrier et al. | |

OTHER PUBLICATIONS

International Search Report, PCT/US 96/11670, dated Jan. 16, 1997.
Steven R. Brant et al., "Cloning tissue distribution, and functional analysis of the human Na+/H+ exhanger isoform, NHE3," American J. Physiol., 269:C198–C206 (1995).
Chung–Ming Tse et al., Molecular Properties, Kinetics and Regulation of Mammalian Na+ /H+Exchangers, Cell Physiol. Biochem. 4:282–300 (1994).
W.A. Hoogerwerf et al., Message Distribution of Three Na+/H+ Exchangers Along the Rabbit Ileal Crypt–Villus Axis and Demonstration that an Epithelial Isoform, NHE2, is Present in Ileal Brush Border Membrane, Intestinal Disorders A239 (Apr. 1994).
Crescence Bookstein et al., Na+/H+ Exchangers, NHE–1 and NHE–3, of Rat Intestine, J. Clin. Invest. 93:106–113 (1994).
S.A. Levine et al., Kinetics and Regulation of Three Cloned Mammalian Na+/H+ Exchangers Stably Expressed in a Fibroblast Cell Line, The Journal of Biological Chemistry 268:25527–25535 (1993).
Daniel Biemesderfer et al., NHE3: a Na+/H+ exchanger isoform of renal brush border, American Journal of Physiology: Renal, Fluid and Elecrolyte Physiology 34:F736–F742 (1993).

C.H. Chris Yun et al., Glucocorticoid Stimulation of Ileal Na+ Absorptive Cell Brush Border Na+/H+ Exchange and Association with an Increase in Message for NHE–3, an Epithelial Na+/H+ Exchanger Isoform, The Journal of Biological Chemistry 268:206–211 (1993).
Steven R. Brant et al., Physical and Genetic Mapping of a Human Apical Epithelial Na+/H+ Exchanger (NHE3) Isoform to Chromosome 5p15.3, Genomics 15:668–672 (1993).
Chung–Ming Tse et al., Functional characteristics of a cloned epithelial Na+/H+ exchanger (NHE3): Resistance to amiloride and inhibition by protein kinase C, Proc. Natl. Acad. Sci. 90:9110–9114 (1993).
John Orlowski, Heterologouis Expression and Functional Properties of Amiloride High Affinity (NHE–1) and Low Affinity (NHE–3) Isoforms of the Rat Na/H Exchanger, The Journal of Biological Chemistry 268:16369–16377 (1993).
C.H. Chris Yun et al., LEU143 In the Putative Fourth Membrane Spanning Domain is Critical for Amiloride Inhibition of an Epithelial Na+/H+ Exchanger Isoform (NHE–2), Biochemical and Biophysical Research Communications 193:532–539 (1993).
Chung–Ming Tse et al., Cloning and Expression of a Rabbit cDNA Encoding a Serum–activated Ethylisopropylamiloride–resistant Epithelial Na+/H+ Exchanger Isoform (NHE–2), The Journal of Biological Chemistry 268:11917–11924 (1993).
Laurent Counillon et al., A point mutation of the Na+/H+ exchanger gene (NHE1) and amplification of the mutated allete confer amiloride resistance upon chronic acidosis, Proc. Natl. Acad. Sci. 90:4508–4512 (1993).
Ming Tse et al., Structure/Function Studies of the Epithelial Isoforms of the Mammalian Na+/H+ Exchanger Gene Family, J. Membrane Biol, 135:93–108 (1993).
Chung–Ming Tse et al., Cloning and Sequencing of a Rabbit cDNA Encoding an Intestinal and Kidney–specific Na+/H+ Exchanger Isoform (NHE–3), The Journal of Biological Chemistry 267:9340–9346 (1992).
W. Richard McCombie et al., Rapid and reliable fluorescent cycle sequencing of double–stranded templates, DNA Sequence—J. DNA Sequencing and Mapping 2:289–296 (1992).
Zafar Zamir et al., Sodium Transport in Human Intestinal Basolateral Membrane Vesicles, Gastroenterology 103:1817–1822 (1992).

(List continued on next page.)

*Primary Examiner*—Gary L. Kunz
*Assistant Examiner*—Jegatheesan Seharaseyon
(74) *Attorney, Agent, or Firm*—Browdy and Neimark, P.L.L.C.

(57) ABSTRACT

This invention presents the cloning and characterization of human NHE3. It sets forth the entire coding region of the human NHE3 cDNA as well as the encoded protein, an 834 amino acid protein with a calculated relative molecular weight of 92,906.

7 Claims, 9 Drawing Sheets

OTHER PUBLICATIONS

Franck Borgese et al., Cloning and expression of a cAMP-activated Na+/H+ exchanger: Evidence that the cytoplasmic domain mediates hormonal regulation, Proc. Natl. Acad. Sci. 89:6765–6769 (1992).

Chung–Ming Tse et al., Cloning and Sequencing of a Rabbit cDNA Encoding an intestinal and Kidney–specific Na$^+$/H$^+$ Exchanger Isoform (NHE–3), Journal of Biological Chemistry, 267:9340–9346 (1992).

J.S. Tung et al., PCR Amplification of Specific Sequences from a cDNA Library, PCR Technology: Principles and Applications for DNA Amplification, 99–104 (1992).

S. Harguindey et al., The Na+/H+ Antiporter in Oncology in the Light of the Spontaneous Regression of Cancer and Cell Metabolism, Medical Hypotheses 39:229–237 (1992).

John Orlowski et al., Molecular Cloning of Putative Members of the Na/H Exchanger Gene Family, The Journal of Biological Chemistry, 267:9331–9339 (1992).

Shigeo Wakabayashi et al., The Na+/H+ antiporter cytoplasmic domain mediates growth factor signals and controls "H+–sensing", Proc. Natl. Acad. Sci. 89:2424–2428 (1992).

L. Domenjoud et al., On the expression of protamine genes in the testis of man and other mammals, Androlocia, 23:333–337 (1991).

C. Ming Tse et al., Molecular cloning and expression of a cDNA encoding the rabbit ileal villus cell basolateral membrane Na+/H+ exchanger, The EMBO Journal 10:1957–1967 (1991).

Sari Acra et al., Increased Na+–H+ Exchangers in Jejunal Brush Border Membrane Vesicles of Spontaneously Hypertensive Rats, Gastroenterology 101:430–436 (1991).

R. Tyler Miller et al., Structure of the 5'–Flanking Regulatory Region and Gene for the Human Growthh Factor–activatable Na/H Exchanger NHE–1, The Journal of Biological Chemistry 266:10813–10819 (1991).

Richard P. Lifton et al., Cloning of the Human Genomic Amiloride–Sensitive Na+/H+ Antiporter Gene, Identification of Genetic Polymorphisms, and Localization on the Genetic Map of Chromosome 1p, Genomics 7:131–135 (1990).

Richard P. Rood et al., Regulation of Small Intestinal Na$^+$ Absorption by Protein Kinases: Implications for Therapy of Diarrheal Diseases, Viewpoints on Digestive Diseases, 22:1–6 (1990).

Gabriel A. Morduchawicz et al., Increased Na+/H+ antiport activity in the renal brush border membrane of SHR, Kidney International 36:576–581 (1989).

Claude Sardet et al., Molecular Cloning, Primary Structure, and Expression of the Human Growth Factor —Activatable Na+/H+ Antiporter, Cell 56:271–280 (1989).

H.M. Berschneider et al., Altered intestinal chloride transport in cystic fibrosis, The FASEB Journal 2:2625–2629 (1988).

J.G. Kleinman et al., Na+ and H+ transport in human jejunal brush–border membrane vesicles, Am. J. Physiol. 255:G206–G211 (1988).

Louis Simchowitz et al., Intracellular Acidification–induced Alkali Metal Cation/H+ Exchange in Human Neutrophils, J. Gen. Physiol. 90:737–762 (1987).

Marilyn Kozak, An analysis of 5'–noncoding sequences from 699 vertebrate messenger RNAs, Nucleic Acids Research, 15:8125–8132 (1987).

Pamela C. Yelick et al., Mouse Protamine 2 is Synthesized as a Precursor whereas Mouse Protamine 1 is Not, Molecular and Cellular Biology 7:2173–2179 (1987).

Mark Donowitz et al., Regulation of Mammalian Small Intestinal Electrolyte Secretion, Physiology of the Gastrointestinal Tract 2:1351–1388 (1987).

Lloyd M. Smith et al., Fluorescence detection in automated DNA sequence analysis, Nature 321:674–678 (1986).

Rex L. Mahnensmith et al., The Plasma Membrane Sodium–Hydrogen Exchanger and its Role in Physiological and Pathophysiological Processes, Circulation Research 56:773–788 (1985).

Roy Knickelbein et al., Sodium and chloride transport across rabbit ileal brush border. II. Evidence for CI–HCO$_3$ exchange and mechanism of coupling, Am. J. Physiol. 249:G236–G245 (1985).

I.W. Booth et al., Defective Jejunal Brush–Border Na+/H+ Exchange: A Cause of Congenital Secretory Diarrhoea, The Lancet 1:1066–1069 (1985).

Roy Knickelbein et al., Sodium and chloride transport across rabbit ileal brush border. I. Evidence for Na–H exchange, Am. J. Physiol. 245:G504–G510 (1983).

Peter S. Aronson, Mechanisms of active H+ secretion in the proximal tubule, Am. J. Physiol. 245: F647–F659 (1983).

J. Michael Freiberg et al., Glucocorticoids increase the Na+–H+ exchange and decreases the Na+ gradient–dependent phosphate–uptake systems in renal brush border membrane vesicles, Proc. Natl. Acad. Sci. 79:4932–4936 (1982).

F. Sanger et al., DNA sequencing with chain–terminating inhibitors, Biochemistry, 74:5463–5467 (1977).

```
RABBIT  NHE3    -36  ATGCGCGTCGGGCCCCGGCGCTGA  -13
RAT     NHE3    -33  ATGCGTGTCGGCTCCTGGAGCTGA  -10
                     ****  ****   **  **  ****
```

```
                                                     GCAGGCGGCA   -1
     ATGTGGGGACTCGGGGCCCGGGGCCCCGACCGGGGGCTGCTGCTGGCGCTGGCG       54
  1  M  W  G  L  G  A  R  G  P  D  R  G  L  L  L  A  L  A
     CTGGGCGGGCTGGCGCGGGCCGGGGGCGTCGAGGTGGAGCCCGGCGGCGCGCAC      108
 19  L  G  G  L  A  R  A  G  G  V  E  V  E  P  G  G  A  H
     GGCGAGAGCGGGGGCTTCCAGGTGGTCACCTTCGAGTGGGCCCACGTGCAGGAT      162
 37  G  E  S  G  G  F  Q  V  V  T  F  E  W  A  H  V  Q  D
     CCCTACGTCATCGCGCTCTGGATCCTCGTGGCCAGCTTGGCCAAGATCGGGTTC      216
 55  P  Y  V  I  A  L  W  I  L  V  A  S  L  A  K  I  G  F
     CACCTGTCCCACAAGGTCACCAGCGTGGTTCCCGAGAGCGCCCTGCTCATCGTG      270
 73  H  L  S  H  K  V  T  S  V  V  P  E  S  A  L  L  I  V
     CTGGGCCTGGTGCTGGGCGGCATCGTCTGGGCGGCCGACCACATCGCGTCCTTC      324
 91  L  G  L  V  L  G  G  I  V  W  A  A  D  H  I  A  S  F
     ACACTGACGCCCACCGTCTTCTTCTTCTACCTGCTGCCCCCCATCGTGCTGGAC      378
109  T  L  T  P  T  V  F  F  F  Y  L  L  P  P  I  V  L  D
     GCCGGCTACTTCATGCCCAACCGCCTCTTCTTCGGCAACCTGGGGACCATCCTG      432
127  A  G  Y  F  M  P  N  R  L  F  F  G  N  L  G  T  I  L
     TTGTACGCCGTCGTGGGTACCGTGTGGAACGCGGCCACCACCGGGCTGTCCCTC      486
145  L  Y  A  V  V  G  T  V  W  N  A  A  T  T  G  L  S  L
     TACGGCGTCTTCCTCAGTGGGCTCATGGGCGACCTGCAGATTGGGCTGCTGGAC      540
163  Y  G  V  F  L  S  G  L  M  G  D  L  Q  I  G  L  L  D
     TTCCTCCTGTTTGGCAGCCTCATGGCGGCTGTGGACCCGGTGGCCGTCCTGGCC      594
181  F  L  L  F  G  S  L  M  A  A  V  D  P  V  A  V  L  A
     GTGTTTGAGGAGGTCCATGTCAACGAGGTCCTGTTCATCATCGTCTTCGGGGAG      648
199  V  F  E  E  V  H  V  N  E  V  L  F  I  I  V  F  G  E
     TCGCTGCTGAACGACGCAGTCACCGTGGTTCTGTACAATGTGTTTGAATCTTTC      702
217  S  L  L  N  D  A  V  T  V  V  L  Y  N  V  F  E  S  F
     GTGGCGCTGGGAGGTGACAACGTGACTGGCGTGGACTGCGTGAAGGGCATAGTG      756
235  V  A  L  G  G  D  N  V  T  G  V  D  C  V  K  G  I  V
     TCCTTCTTCGTGGTGAGCCTGGGGGGCACGCTGGTGGGGGTGGTCTTCGCCTTC      810
253  S  F  F  V  V  S  L  G  G  T  L  V  G  V  V  F  A  F
     CTGCTGTCGCTGGTGACGCGCTTCACCAAGCATGTGCGTATCATCGAGCCCGGC      864
271  L  L  S  L  V  T  R  F  T  K  H  V  R  I  I  E  P  G
     TTCGTGTTCATCATCTCCTACCTGTCCTACCTGACGTCCGAGATGCTGTCGCTG      918
289  F  V  F  I  I  S  Y  L  S  Y  L  T  S  E  M  L  S  L
     TCGGCCATCCTCGCCATCACCTTCTGTGGCATCTGCTGTCAGAAGTATGTGAAG      972
307  S  A  I  L  A  I  T  F  C  G  I  C  C  Q  K  Y  V  K
     GCCAACATCTCGGAGCAGTCGGCCACCACCGTGCGCTACACCATGAAGATGCTG     1026
325  A  N  I  S  E  Q  S  A  T  T  V  R  Y  T  M  K  M  L
     GCCAGCAGCGCCGAGACCATCATCTTCATGTTCCTGGGTATCTCGGCCGTGAAC     1080
343  A  S  S  A  E  T  I  I  F  M  F  L  G  I  S  A  V  N
     CCGTTCATCTGGACCTGGAACACGGCCTTCGTGCTCCTGACGCTGGTCTTCATC     1134
361  P  F  I  W  T  W  N  T  A  F  V  L  L  T  L  V  F  I
     TCCGTGTACCGGGCCATCGGTGTGGTCCTGCAGACCTGGCTTCTGAACCGCTAC     1188
379  S  V  Y  R  A  I  G  V  V  L  Q  T  W  L  L  N  R  Y
     CGCATGGTGCAGCTGGAGCCCATTGACCAGGTGGTCCTGTCCTACGGGGGCCTG     1242
397  R  M  V  Q  L  E  P  I  D  Q  V  V  L  S  Y  G  G  L
     CGCGGGGCCGTGGCCTTTGCCCTGGTGGTGCTTCTGGATGGAGACAAGGTCAAG     1296
415  R  G  A  V  A  F  A  L  V  V  L  L  D  G  D  K  V  K
     GAGAAGAACCTGTTCGTCAGCACCACCATCATCGTAGTGTTCTTCACCGTCATC     1350
433  E  K  N  L  F  V  S  T  T  I  I  V  V  F  F  T  V  I
```

FIG. 3A

```
     TTCCAGGGCCTGACCATCAAGCCTCTGGTGCAGTGGCTGAAGGTGAAGAGGAGC 1404
451  F  Q  G  L  T  I  K  P  L  V  Q  W  L  K  V  K  R  S
     GAGCACCGGGAACCTCGGCTCAACGAGAAGCTGCACGGCCGCGCTTTCGACCAC 1458
469  E  H  R  E  P  R  L  N  E  K  L  H  G  R  A  F  D  H
     ATCCTCTCGGCCATCGAGGACATATCCGGACAGATCGGGCACAATTATCTCAGA 1512
487  I  L  S  A  I  E  D  I  S  G  Q  I  G  H  N  Y  L  R
     GACAAGTGGTCCCACTTCGACAGGAAGTTCCTCAGCAGGGTCCTCATGAGACGG 1566
505  D  K  W  S  H  F  D  R  K  F  L  S  R  V  L  M  R  R
     TCGGCCCAGAAGTCTCGAGACCGGATCCTGAATGTCTTCCACGAGCTGAACCTG 1620
523  S  A  Q  K  S  R  D  R  I  L  N  V  F  H  E  L  N  L
     AAGGATGCCATCAGCTACGTGGCTGAGGGAGAGCGCCGCGGGTCCCTGGCCTTC 1674
541  K  D  A  I  S  Y  V  A  E  G  E  R  R  G  S  L  A  F
     ATCCGCTCCCCCAGCACCGACAACGTGGTCAACGTGGACTTCACGCCACGATCG 1728
559  I  R  S  P  S  T  D  N  V  V  N  V  D  F  T  P  R  S
     TCCACCGTGGAGGCCTCTGTCTCCTACCTCCTGAGAGAAAATGTCAGCGCTGTC 1782
577  S  T  V  E  A  S  V  S  Y  L  L  R  E  N  V  S  A  V
     TGCCTGGACATGCAGTCTCTGGAGCAGCGACGGCGGAGCATCCGGGACGCGGAG 1836
595  C  L  D  M  Q  S  L  E  Q  R  R  R  S  I  R  D  A  E
     GACATGGTCACGCACCACACGCTACAGCAGTACCTGTACAAGCCGCGGCAGGAG 1890
613  D  M  V  T  H  H  T  L  Q  Q  Y  L  Y  K  P  R  Q  E
     TACAAGCATCTGTACAGCCGACACGAGCTCACGCCCACGGAGGACGAGAAACAG 1944
631  Y  K  H  L  Y  S  R  H  E  L  T  P  T  E  D  E  K  Q
     GACCGGGAAATCTTCCACAGGACCATGCGGAAGCGCCTGGAGTCCTTCAAGTCG 1998
649  D  R  E  I  F  H  R  T  M  R  K  R  L  E  S  F  K  S
     ACCAAGCTGGGGCTCAACCAGAACAAGAAGGCAGCCAAGCTGTACAAGCGGGAG 2052
667  T  K  L  G  L  N  Q  N  K  K  A  A  K  L  Y  K  R  E
     CGTGCCCAGAAGCGGAGAAACAGCAGCATCCCCAATGGGAAGCTGCCCATGGAG 2106
685  R  A  Q  K  R  R  N  S  S  I  P  N  G  K  L  P  M  E
     AGCCCTGCGCAGAATTTCACCATCAAGGAGAAAGACTTGGAACTTTCAGACACC 2160
703  S  P  A  Q  N  F  T  I  K  E  K  D  L  E  L  S  D  T
     GAGGAGCCCCCCAACTATGATGAGGAGATGAGTGGGGGGATCGAGTTCCTGGCT 2214
721  E  E  P  P  N  Y  D  E  E  M  S  G  G  I  E  F  L  A
     AGTGTCACCAAGGACACAGCGTCCGACTCCCCTGCAGGAATTGACAACCCTGTG 2268
739  S  V  T  K  D  T  A  S  D  S  P  A  G  I  D  N  P  V
     TTTTCTCCGGACGAGGCCCTGGACCGCAGCCTCCTGGCCAGGCTGCCGCCCTGG 2322
757  F  S  P  D  E  A  L  D  R  S  L  L  A  R  L  P  P  W
     CTGTCTCCCGGGGAGACGGTGGTCCCCTCGCAGAGGGCCCGCACGCAGATTCCC 2376
775  L  S  P  G  E  T  V  V  P  S  Q  R  A  R  T  Q  I  P
     TACTCTCCCGGCACCTTCCGCCGCCTGATGCCCTTCCGCCTCAGCAGCAAGTCC 2430
793  Y  S  P  G  T  F  R  R  L  M  P  F  R  L  S  S  K  S
     GTGGACTCCTTCCTGCAGGCAGACGGCCCCGAGGAGCGGCCCCCCGCCGCCCTC 2484
811  V  D  S  F  L  Q  A  D  G  P  E  E  R  P  P  A  A  L
     CCCGAGTCCACACACATGTGACACCGGCTCCGACACGCCGCTAACCGGCCGCTC 2538
829  P  E  S  T  H  M  *
     GTCCCCGCGCCACGGTCCGCCCACCGCCGCCGCCGC                   2574
```

*FIG. 3B*

```
                      m1
HUMNHE3   MWGLGARGPDRGLLLALALG--GLARAGGVEVEPGGAHGESGGFQVVTFEWAHVQDP   55
RATNHE3   MWH-PALGPGWKPLLALAVAVTSLRGVRGIEEEPNSG----GSFQIVTFKWHHVQDP   52
RABNHE3   MSGRGGCGPCWGLLLALVLALGALPWTQGAEQEH---HDEIQGFQIVTFKWHHVQDP   54
            *  .  **  .  ****. . .  *  . * * *.      ** *** * *****
                     m2                         m3
HUMNHE3   YVIALWILVASLAKIGFHLSHKVTSVVPESALLIVLGLVLGGIVWAADHIASFTLTP   112
RATNHE3   YIIALWILVASLAKIVFHLSHKVTSVVPESALLIVLGLVLGGIVWAADHIASFTLTP   109
RABNHE3   YIIALWVLVASLAKIVFHLSHKVTSVVPESALLIVLGLVLGGIVLAADHIASFTLTP   111
          * .****.*******.********************************.***********
                   m4                      m5
HUMNHE3   TVFFFYLLPPIVLDAGYFMPNRLFFGNLGTILLYAVVGTVWNAATTGLSLYGVFLSG   169
RATNHE3   TLFFFYLLPPIVLDAGYFMPNRLFFGNLGTILLYAVIGTIWNAATTGLSLYGVFLSG   166
RABNHE3   TVFFFYLLPPIVLDAGYFMPNRLFFSNLGSILLYAVVGTVWNAATTGLSLYGVFLSG   168
          *.*********************** .***.*****.**.**********************
                           m5a                      m5b
HUMNHE3   LMGDLQIGLLDFLLFGSLMAAVDPVAVLAVFEEVHVNEVLFIIVFGESLLNDAVTVV   226
RATNHE3   LMGELKIGLLDFLLFGSLIAAVDPVAVLAVFEEVHVNEVLFIIVFGESLLNDAVTVV   223
RABNHE3   IMGELKIGLLDFLLFGSLIAAVDPVAVLAVFEEVHVNEVLFIIVFGESLLNDAVTVV   225
          .** * *********** ***************************************
                                            m6
HUMNHE3   LYNVFESFVALGGDNVTGVDCVKGIVSFFVVSLGGTLVGVVFAFLLSLVTRFTKHVR   283
RATNHE3   LYNVFESFVTLGGDAVTGVDCVKGIVSFFVVSLGGTLVGVIFAFLLSLVTRFTKHVR   280
RABNHE3   LYNVFQSFVTLGGDKVTGVDCVKGIVSFFVVSLGGTLVGVVFAFLLSLVTRFTKHVR   282
          ***** .*** **** ************************ . ****************
                          m7
HUMNHE3   IIEPGFVFIISYLSYLTSEMLSLSAILAITFCGICCQKYVKANISEQSATTVRYTMK   340
RATNHE3   IIEPGFVFVISYLSYLTSEMLSLSAILAITFCGICCQKYVKANISEQSATTVRYTMK   337
RABNHE3   VIEPGFVFIISYLSYLTSEMLSLSSILAITFCGICCQKYVKANISEQSATTVRYTMK   339
          .******. ************** ***********************************
                m8                   M9
HUMNHE3   MLASSAETIIFMFLGISAVNPFIWTWNTAFVLLTLVFISVYRAIGVVLQTWLLNRYR   397
RATNHE3   MLASGAETIIFMFLGISAVDPVIWTWNTAFVLLTLVFISVYRAIGVVLQTWILNRYR   394
RABNEE3   MLASGAETIIFMFLGISAVDPLIWTWNTAFVRLTLLFVSVFRAIGVVLQTWLLNRYR   396
          ****.*********** .* ********* . *** * ** .***********.****
                                              m10
HUMNHE3   MVQLEPIDQVVLSYGGLRGAVAFALVVLLDGDKVKEKNLFVSTTIIVVFFTVIFQGL   454
RATNHE3   MVQLETIDQVVMSYGGLRGAVAYALVVLLDEKKVKEKNLFVSTTLIVVFFTVIFQGL   451
RABNHE3   MVQLELIDQVVMSYGGLRGAVAFALVALLDGNKVKEKNLFVSTTIIVVFFTVIFQGL   453
          ***** ***** ********** ***.***. **********. **************
```

*FIG. 4A*

```
HUMNHE3   TIKPLVQWLKVKRSEHREPRLNEKLHGRAFDHILSAIEDISGQIGHNYLRDKWSHFD   511
RATNHE3   TIKPLVQWLKVKRSEQREPKLNEKLHGRAFDHILSAIEDISGQIGHNYLRDKWSNFD   508
RABNHE3   TIKPLVQWLKVKRSEHREPKLNEKLHGRAFDHILSAIEDISGQIGHNYLRDKWANFD   510
          *************.***.**************************** **

HUMNHE3   RKFLSRVLMRRSAQKSRDRILNVFHELNLKDAISYVAEGERRGSLAFIRSPSTDNVV   568
RATNHE3   RKFLSKVLMRRSAQKSRDRILNVFHELNLKDAISYVAEGERRGSLAFIRSPSTDNMV   565
RABNHE3   RRFLSKLLMRQSAQKSRDRILNVFHELNLKDAISYVTEGERRGSLAFIRSPSTDNMV   567
          *.***..***.****************************.*****************.*

HUMNHE3   NVDF-TPRSSTVEASVSYLLRENVSAVCLDMQSLEQRRRSIRDAEDMVTHHTLQQYL   624
RATNHE3   NVDFSTPRPSTVEASVSYFLRENVSAVCLDMQSLEQRRRSIRDTEDMVTHHTLQQYL   622
RABNHE3   NVDFSTPRPSTVEASVSYLLRESASAVCLDMQSLEQRRRSVRDAEDVITHHTLQQYL   624
          **** *** ********.***.*********************.**.**.*********

HUMNHE3   YKPRQEYKHLYSRHELTPTEDEKQDREIFHRTMRKRLESFKSTKLGLNQNKKAAKLY   681
RATNHE3   YKPRQEYKHLYSRHELTPNEDEKQDKEIFHRTMRKRLESFKSAKLGINQNKKAAKLY   679
RABNHE3   YKPRQEYKHLYSRHVLSPSEDEKQDKEIFHRTMRKRLESFKSAKLGLGQSKKATKHK   681
          **************  * .*******.**************** ***.*.***.*.*

HUMNHE3   K-RERAQKRRNSSIPNGKLPMESPAQNFTIKEKDLELSDTEEPPNY--DEEMSGGIE   735
RATNHE3   K-RERAQKRRNSSIPNGKLPMENLAHNFTIKEKDLELSEPEEATNY---EEISGGIE   732
RABNHE3   RERERAQKRRNSSVPNGKLPLDSPRYGLTLKERELELSDPEEAPDYYEAEKMSGGIE   738
           .***********.******...  ...**.***.**..**...*  *..*****

HUMNHE3   FLASVTKDTASDSPAGIDNPVFSPDEALDRSLLARLPPWLSPGETVVPSQRARTQIP   792
RATNHE3   FLASVTKDVASDSGAGIDNPVFSPDEDLDPSILSRVPPWLSPGETVVPSQRARVQIP   789
RABNHE3   FLASVTKVSTSDSPAGIDNPVFSPDEDLAPSLLARVPPWLSPGEAVVPSQRARVQIP   795
          *******  ***.************.*. *..*.*.***********.*********.***

HUMNHE3   YSPGTFRRLMPFRLSSKSVDSFLQADGPEERPPAALPESTHM   834
RATNHE3   NSPSNFRRLTPFRLSNKSVDSFLQADGPEEQLQPASPESTHM   831
RABNHE3   YSPGNFRRLAPFRLSNKSVDSFLLAEDGAEH-----PESTHM   832
          .** .****.*****.*******.*.** *     ******
```

HUMAN NHE3 PROTEIN AND NON-HUMAN CELLS EXPRESSING SAME

CROSS-REFERENCE TO RELATED APPLICATIONS

This application is a divisional of application Ser. No. 08/677,734 filed Jul. 10, 1996, now U.S. Pat. No. 5,871,919, which claims the benefit under 35 USC §119(e)(1) to provisional application Ser. No. 60/001,061 filed on Jul. 11, 1995.

BACKGROUND

The $Na^+/H^+$ exchangers, or antiporters, are plasma membrane transport proteins that exchange extracellular $Na^+$ for intracellular $H^+$ and are found in virtually all animals. In fact, all eukaryotic cells studied, including yeast, the worm (*Caenorhabditis elegans*), and crustaceans, have exhibited plasma membrane $Na^+/H^+$ exchangers (also called NHE) which exchange these ions at a ratio of 1:1. Prokaryotes have functionally similar $Na^+/H^+$ exchanger proteins which also regulate intracellular $Na^+$ ion concentration and pH, and exchange one intracellular $Na^+$ for one $H^+$.

In eukaryotic cells, the plasma membrane $Na^+/H^+$ exchangers have multiple functions, including pH homeostasis, volume regulation, cell proliferation, and transcellular $Na^+$ absorption. In no cell, however, is the $Na^+/H^+$ exchanger the only mechanism for these functions. For instance, pH homeostasis is controlled in most eukaryotic cells by mechanisms including a $Cl^-/HCO_3^-$ exchanger, a $NaHCO_3^-$ co-transporter, a $NA^+$-dependent $Cl^-/HCO_3^-$ exchanger, and multiple mechanisms of $H^+$ extrusion.

Nonetheless, understanding the $Na^+/H^+$ exchanger will greatly increase the understanding of the body's control of ions, and much work has been done on the $Na^+/H^+$ exchanger family. Four mammalian $Na^+/H^+$ exchanger isoforms have been cloned (NHE1-4) (28). Of these, NHE3 appears to be the $Na^+/H^+$ exchanger isoform that is most likely responsible for "brush border" $Na^+/H^+$ exchange activity.

The brush border consists of microvilli, approximately 1 $\mu$ in length and 0.1 $\mu$ in diameter, that protrude from the surface of epithelial cells on the intestine and renal tubules. These microvilli greatly increase the surface area of those cells. Brush border $Na^+/H^+$ exchange activity contributes to transepithelial neutral NaCl absorption (38) in the small intestine, and to $Na^+$ reuptake in the proximal renal tubule (11,12,16). Additionally, brush border $Na^+/H^+$ exchange activity is important in the secretion of acid in the proximal renal tubule (1).

Thus, a malfunctioning $Na^+/H^+$ exchanger affects a body's well being. In chronic metabolic acidosis, chronic renal failure, diabetic nephropathy, and in animal models of essential hypertension, one observes an increase in renal proximal tubule brush border $Na^+/H^+$ exchange activity (16,18). More specifically regarding hypertension, increased $Na^+/H^+$ exchange in the renal proximal tubule or cortical thick ascending limb of Henle would enhance $Na^+$ reabsorption, leading to a defect in renal $Na^+$ excretion (16). It has been shown that defective renal $Na^+$ excretion is a cause in some patients of essential hypertension (16).

Similarly, increased jejunal brush border $Na^+/H^+$ exchange has been shown to be present in animal models of essential hypertension (40). Increased ileal and renal brush border $Na^+/H^+$ exchange activity is an important mechanism for the increased ileal and renal NaCl and water absorption that occurs in response to administration of glucocorticoids (34,41) and thus may, in part, be responsible for common side-effects of glucocorticoid pharmacologic therapy in humans such as hypertension and fluid and salt retention.

Conversely, decreased brush border $Na^+/H^+$ exchange activity is the major mechanism for decreased $Na^+$ and water absorption in most human diarrheal diseases (21). In one familial diarrheal syndrome, congenital sodium diarrhea, there is evidence of a congenital absence of jejunal brush border $Na^+/H^+$ exchange activity (4).

NHE3 is believed to be the $Na^+/H^+$ exchanger that is increased in the above renal diseases and inhibited in diarrheal diseases because the $Na^+/H^+$ exchange activity of NHE3 is most like that of ileal villus cell brush border membranes: it is relatively resistant to $Na^+/H^+$ exchange inhibition by amiloride, and it is the only $Na^+/H^+$ exchanger isoform inhibited and not stimulated by protein kinase C (28). Furthermore, only NHE3 message expression increases in parallel with the increased ileal villus apical $Na^+/H^+$ exchange activity in rabbits treated for 24 h with methylprednisolone (34). Recent immunohistochemical studies and Western analysis have demonstrated that NHE3 is present on the brush border but not the basolateral membranes of ileal villus and ascending colon surface epithelial cells and proximal renal tubules (2,3). Therefore, NHE3 is believed to be the $Na^+/H^+$ exchanger isoform responsible for the characteristic $Na^+/H^+$ exchange activity of the brush border membranes of the mammalian small intestinal, colonic and proximal renal tubule $Na^+$ absorbing cells (14,28).

In addition, activation of plasma membrane $Na^+/H^+$ exchange has been postulated to play an important role in oncogenic transformation, and inhibitors of plasma membrane $Na^+/H^+$ exchange activity have been shown to have antitumoral effects (16,42).

A partial human NHE3 cDNA, clone HKC-3, which encodes 325 amino acids having 94% identity to rabbit NHE3 residues 180–505, has been previously reported (26). Clone HKC-3 has been used to physically and genetically map human NHE3 to chromosome 5p15.3, making NHE3 the most telomeric gene identified on chromosome 5p (6) and proving that the human NHE3 homologue arises from a different gene than human NHE1, mapped to 1p (15). Nonetheless, the existence of the clone did not provide the full DNA sequence of human NHE3 or the protein itself, and there remained in the art a need for that sequence.

SUMMARY OF THE INVENTION

The present invention provides the full cDNA sequence of human NHE3 as well as the deduced amino acid sequence of NHE3. The invention also provides an expression vector comprising the DNA encoding human NHE3, as well as a host cell transformed with the vector. Such a transformed host cell can be used as a screen for drugs that affect the $Na^+/H^+$ exchanger.

BRIEF DESCRIPTION OF THE FIGURES

FIGS. 3A–3B. These figures set forth the nucleotide sequence of the human NHE3 composite cDNA (above)

(SEQ ID NOs:7 and 8) and the deduced amino acid sequence of the protein (below) (SEQ ID NO:9).

FIGS. 4A–4B. These figures demostrate the alignment of the amino acid sequence of human NHE3 (HUMNHE3), (SEQ ID NO:10), rat NHE3 (RATHNE3) (SEQ ID NO:11), and rabbit NHE3 (RABNHE3) (SEQ ID NO:12).

Figure 5A:
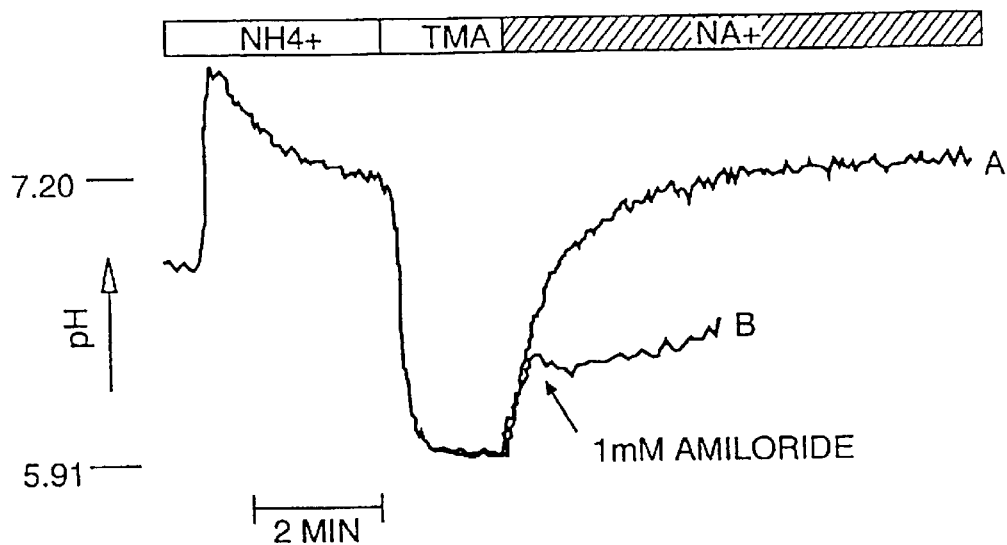
Figure 5B:
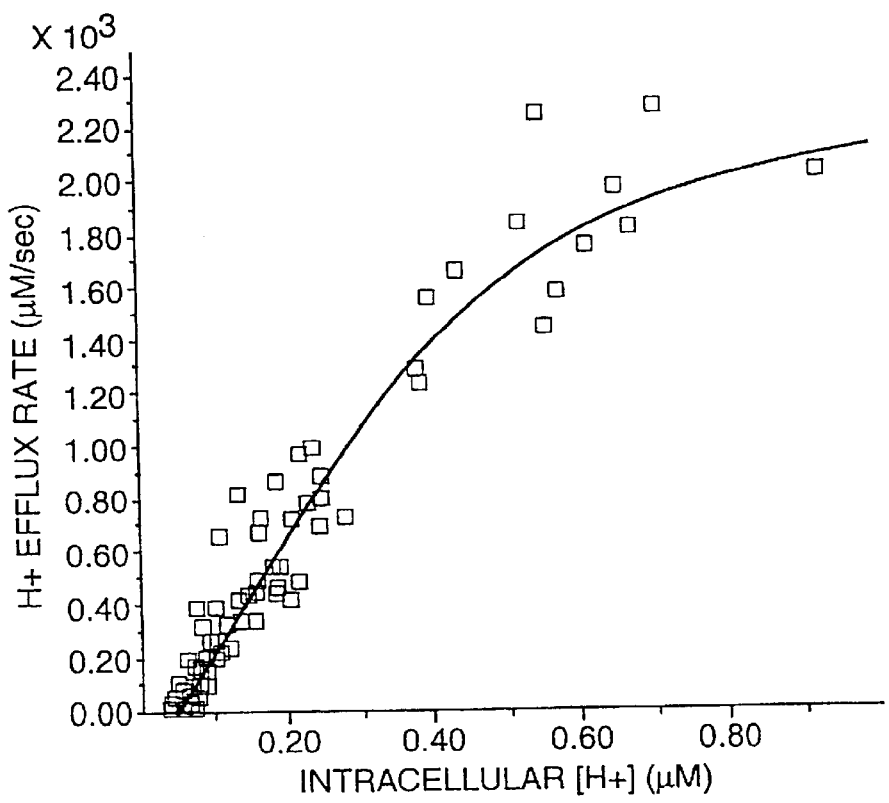

FIGS. 5A–5B. These figures provide a functional characterization of cells stably transfected with human NHE3 cDNA. FIG. 5A sets forth a composite tracing of two representative experiments on $pH_i$ recovery and FIG. 5B demonstrates $H^+$ efflux rate as a function of intracellular $[H^+]$ concentration.

Figures 2, 6:
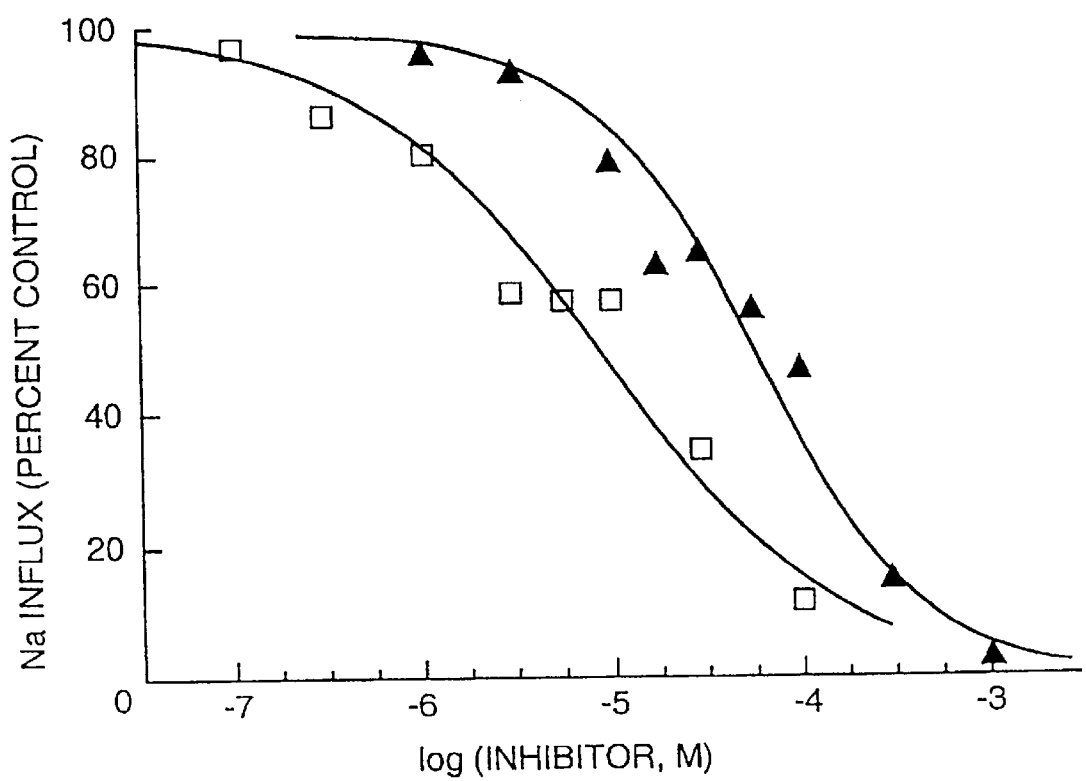
FIG. 2. This figure demonstrates the alignment of the minicistron sequences located in the 5' noncoding regions of rabbit NHE3 (SEQ ID NO:5) and rat NHE3 (SEQ ID NO:6(20, 26).

FIG. 6. This figure sets forth the concentration dependence curves for inhibition of $^{22}Na^+$ (1 mM) uptake in HNHE3/PS-120 cells by amiloride (△) and ethylisopropylamiloride (EIPA) (□).

Figure 7A:
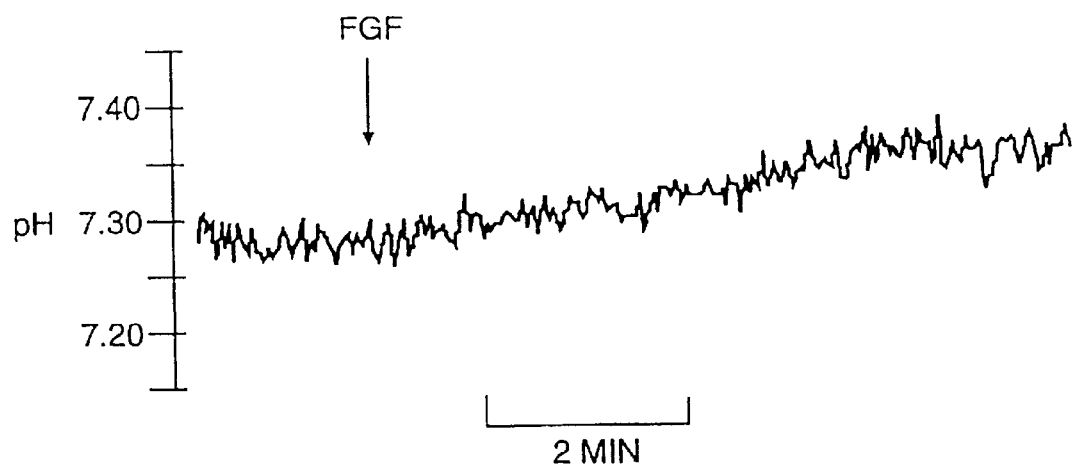
Figure 7B:
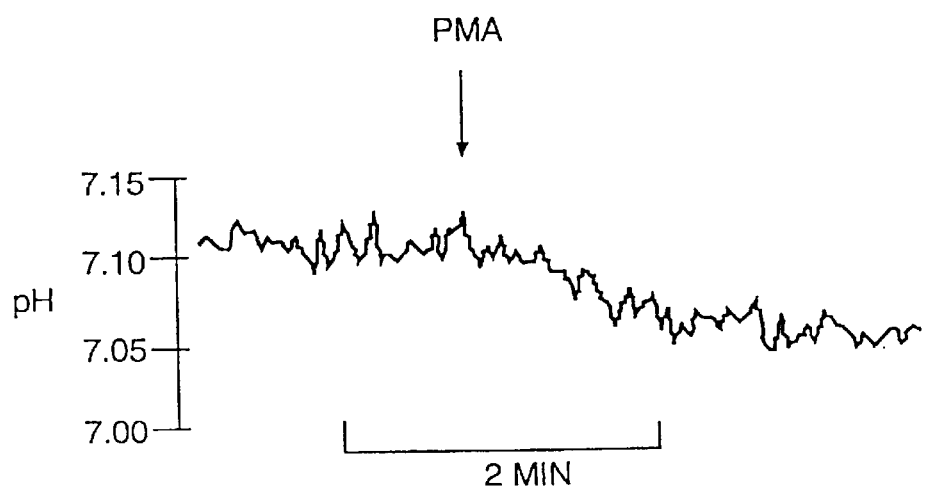

FIGS. 7A–7B. These figures provide tracings from representative experiments on the regulation of human NHE3 at steady state $pH_i$ by either 10 ng/ml FGF (FIG. 7A) or 1.0 μM PMA FIG. 7B.

Figure 8:
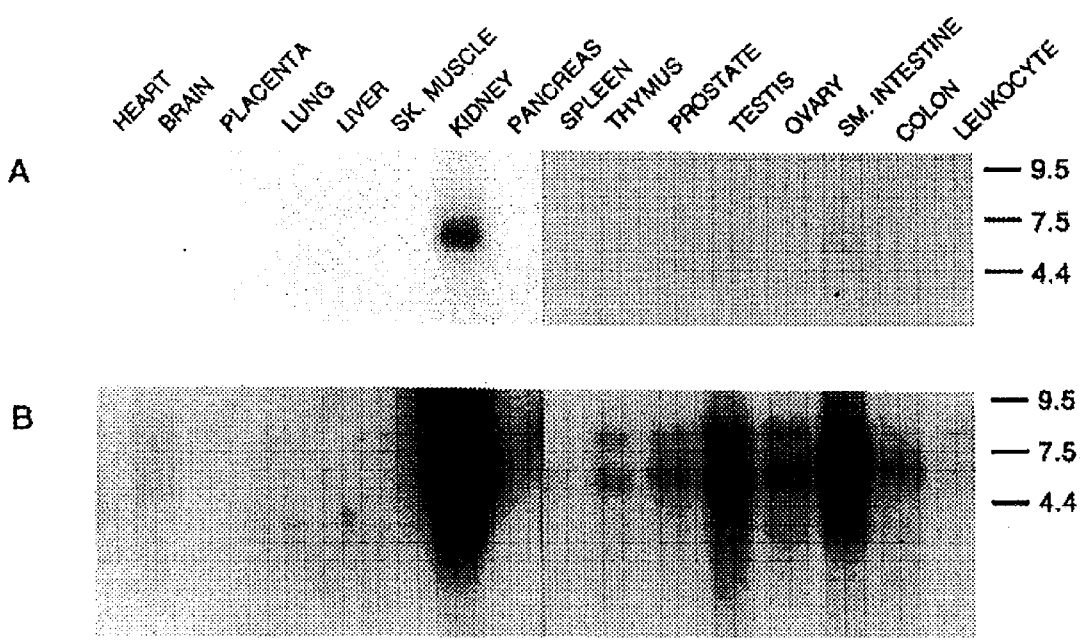

FIG. 8. This figure sets forth a northern blot analysis of expression of NHE3 in human tissues.

DETAILED DESCRIPTION OF THE INVENTION

To obtain the full length human NHE3 gene, we prepared a composite cDNA made up of the DNA of three pieces:

clone HKC-3;

clone HKC-5, another NHE3 clone obtained using HKC-3 as a probe, which overlaps with HKC-3 and contains the entire 3' region of human NHE3; and clone 23-3, obtained using a new method described below. That composite cDNA is set forth in schematically in FIG. 1 while FIG. 3 provides the nucleotide sequence of the human NHE3 composite cDNA (above) and the deduced amino acid sequence (below).

We had previously reported a human NHE3 partial cDNA clone HKC-3 (26) (report providing only the putative amino acid sequence of HKC-3). Colony hybridization screening of the library that yielded HKC-3, as well as two other libraries, did not provide the complete 5' coding nucleotides of the NHE3 full length cDNA. Interestingly, the most 5' nucleotide sequence found was at a location homologous to the most 5' nucleotides of exon 2 of human NHE1, and it is known that a 41.5 Kb intron separates exons 1 and 2 in human NHE1. Subsequent work in our laboratory supports the presence of a large intron segment between exons 1 and 2 that would make obtaining the 5' end difficult. We subsequently also determined that a segment in the 5' region is GC rich, further compounding the difficulty of cloning the 5' end.

Accordingly, we developed a new method to clone the 5' region. We first prepared a degenerate forward primer B8, developed from the sequences encoding minicistrons found in the 5' untranslated regions of both rabbit and rat NHE3 (FIG. 2). We ultimately obtained the remaining 5' coding region (clone 23-3) by reverse transcription/polymerase chain reaction (RT-PCR) of human kidney RNA, based on a reverse primer, B3, derived from HKC-3, and the forward primer B8.

The three pieces provided a composite of human NHE3 cDNA. Thus, an embodiment of the claimed invention is a DNA molecule encoding human NHE3 comprising the nucleotide sequence of FIGS. 3A–3B. Another embodiment of the invention is a DNA molecule, or fragment thereof, encoding human NHE3 comprising the 5' region of the nucleotide sequence of FIGS. 3A–3B.

The invention also includes an expression vector comprising the DNA molecule, or fragment thereof, encoding human NHE3 of FIGS. 3A–3B. A preferable expression vector is pECE. Another aspect of the invention is a host cell transfected with the expression vector containing the claimed DNA. One such host cell is PS120, a fibroblast cell derived from the Chinese hamster lung fibroblast cell line CCL39 that lacks all endogenous $Na^+/H^+$ exchangers.

In another embodiment, the claimed invention includes the protein or polypeptide encoded by the nucleotide sequence of FIGS. 3A–3B; or any fragment thereof.

In an important embodiment, the NHE3 of the invention is the characteristic $Na^+/H^+$ exchanger of the brush border of the kidney and small intestine. Thus, another embodiment of the invention relates to the use of a cell line transformed with NHE3 cDNA as a screen for drugs that affect the brush border of the kidney or small intestine. In a preferred embodiment, the transformant is PS120/NHE3.

Another unexpected finding of the invention is the tissue distribution of the claimed human NHE3. Unlike the limited presence of rat and rabbit NHE3 in kidney, stomach, some intestinal tissues, and brain, the claimed human NHE3 has been detected in a variety of epithelial and nonepithelial human tissues, ranging as follows: kidney>>small intestine>>testes>ovary>colon= prostate>thymus>peripheral leukocyte= brain>spleen>placenta, and including endothelial cells. No NHE3 was detected in the heart, lung, liver, skeletal muscle, or pancreas. Thus, in another embodiment, the invention relates to the use of a cell line transformed with NHE3 cDNA as a screen for drugs that affect cells other than the epithelium of the kidney or small intestine, such as the endothelium of man. In a preferred embodiment, the transformant is PS120/NHE3, especially in screening for drugs which are useful to treat or cure hypertension and other medical conditions, including but not limited to those as noted above.

The practice of the present invention will employ the conventional terms and techniques of molecular biology, microbiology, recombinant DNA, and biochemistry that are within the ordinary skill of those in the art. See, for example, Sambrook, et al., MOLECULAR CLONING: A LABORATORY MANUAL, 2nd ed. Cold Spring Harbor Laboratory Press (1985).

Nonetheless, we offer the following basic background information. DNA, deoxyribonucleic acid, consists of two complementary strands of nucleotides, which include the four different bases compounds, adenine (A), thymine (T), cytosine (C), and guanine (G). A of one strand bonds with T of the other strand while C of one strand bonds to G of the other to form complementary "base pairs", each pair having one base in each strand.

A sequential grouping of three nucleotides (a "codon") codes for one amino acid. Thus, for example, the three nucleotides CAG codes for the amino acid Glutamine. The 20 naturally occurring amino acids, and their one letter codes, are as follows:

| | | |
|---|---|---|
| Alanine | Ala | A |
| Arginine | Arg | R |
| Asparagine | Asn | N |
| Aspartic Acid | Asp | D |
| Asparagine or | Asx | B |

-continued

| | | |
|---|---|---|
| Aspartic acid | | |
| Cysteine | Cys | C |
| Glutamine | Gln | Q |
| Glutamine Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acids comprise proteins. DNA is related to protein as follows:

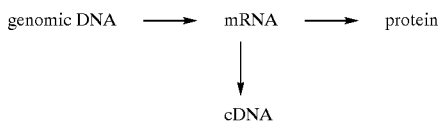

Genomic DNA is all the DNA sequences found in an organism's cell. It is "transcribed" into messenger RNA ("mRNA"). Complementary DNA ("cDNA") is a complementary copy of mRNA made in the laboratory by reverse transcription of mRNA. Unlike genomic DNA, both mRNA and cDNA contain only the protein-encoding regions of the DNA, the so-called "exons." Genomic DNA also includes "introns" which do not encode proteins.

Collections or "libraries" of genomic DNA and cDNA may be constructed in the laboratory or obtained from commercial sources. The DNA molecules present in the libraries may be of unknown function and chemical structure, and the proteins they encode may also be unknown. Nonetheless, one can attempt to retrieve specific desired DNA molecules from the libraries by screening the libraries with a gene probe. A gene probe bears a sequence that is complementary to the sequence of interest and will, accordingly, bond or "hybridize" with the sequence.

Once retrieved, the DNA can be sequenced using techniques that are standard in the art, such as Sanger's dideoxy termination procedure. To orient oneself on the DNA structure, it is referred to as having a 5' end and a 3' end based on the structure of the nucleotides that make up the DNA.

DNA can be cut, spliced, and otherwise manipulated using "restriction enzymes" that cut DNA at certain known sites and DNA polymerases that join DNA. Such techniques are well known to those in the art, as set forth in texts such as Sambrook, et al., MOLECULAR CLONING: A LABORATORY MANUAL, 2nd ed. Cold Spring Harbor Laboratory Press (1985).

DNA of a specific size and sequence can then be inserted into a "replicon", any genetic element, such as a plasmid, cosmid, or virus, that is capable of replication under its own control. A "recombinant vector" or "expression vector" is a replicon into which a DNA segment is inserted so as to allow for expression of the DNA, i.e., production of the protein encoded by the DNA. Expression vectors may be constructed in the laboratory, obtained from other laboratories, or purchased from commercial sources. Expression vectors that would be suitable for use in this invention include pECE and pMAMneo.

The recombinant vector (known by various terms in the art) may be introduced into a host by a process generically known as "transformation". Transformation means the transfer of an exogenous DNA segment by a number of methods, including infection, direct uptake, transduction, F-mating, microinjection, or electroporation into a host cell.

Host cells, known variously as recombinant host cells, cells, and cell culture, include microorganisms, insect cells, and mammalian cells. As those in the art recognize, the expression of the DNA segment by the host cell requires the regulatory sequences. The regulatory sequences vary according to the host cell employed, but include, for example, in prokaryotes, a promoter, ribosomal binding site, and/or a transcription termination site. In eukaryotes, such regulatory sequences include a promoter and/or a transcription termination site.

The DNA may be expressed as a polypeptide of any length such as peptides, oligopeptides, and proteins. Polypeptides also include translational modifications such as glycosylations, acetylations, phosphoralations, and the like.

Having provided this background information, we now describe preferred aspects of the invention.

We had previously described the cloning of a partial cDNA isolated from a human kidney cortex library, clone HKC-3, that had 94% amino acid identity to the previously characterized rabbit NHE3 $Na^+/H^+$ exchanger isoform (26). In the work underlying this invention, we have determined that HKC-3 represents a cDNA fragment of a functioning human NHE3 $Na^+/H^+$ exchanger isoform.

To extend the human cDNA beyond that of HKC-3, we reprobed the human kidney cortex library using HKC-3 as a probe. We identified an additional NHE3 clone, designated HKC-5, which overlaps with clone HKC-3 and contains the entire 3' coding and noncoding regions of human NHE3. Neither, however, provided the 5' coding region.

We ultimately obtained that region using reverse transcription/polymerase chain reaction (RT-PCR) of human kidney RNA, based on a reverse primer B3, derived from HKC-3, and a forward primer, B8, a degenerate primer derived from the 5' region of both rabbit and rat NHE3 (FIG. 2). The RT-PCR amplification yielded clone 23-3 which contains the sought-after 5' coding sequence of human NHE3.

Figure 1:
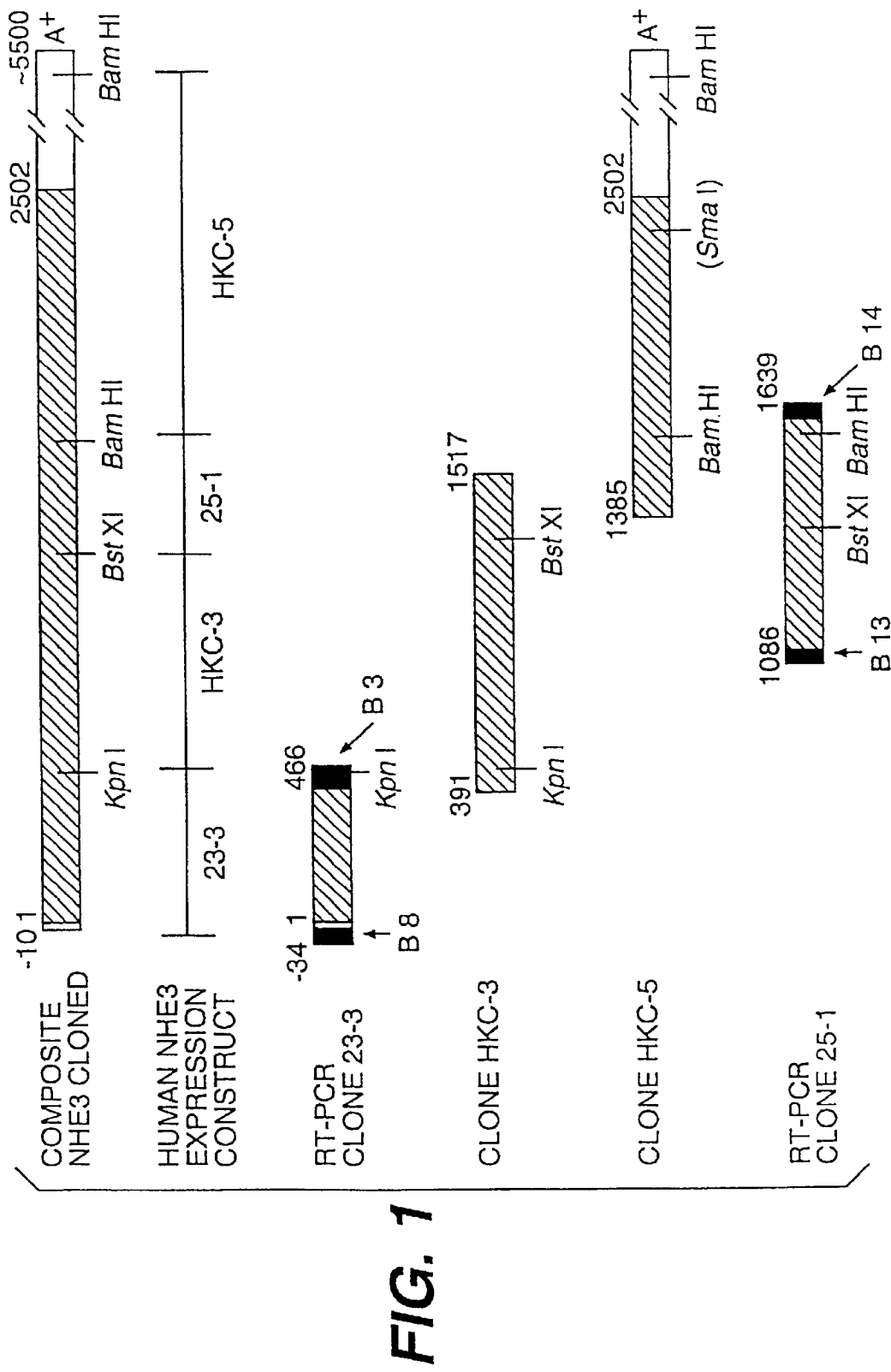
FIG. 1. This figure provides a schematic representation of human NHE3 composite cDNA and partial cDNA clones used in the cloning of human NHE3.

We created a composite human NHE3 based on these pieces. FIG. 1 provides a schematic representation of the human NHE3 composite while FIGS. 3A–3B provide the nucleotide sequence of the human NHE3 composite cDNA and deduced amino acid sequence.

The deduced amino acid sequence, based on the identity of the three-nucleotide codon, of human NHE3 is 834 residues and the calculated relative molecular weight is 92,906. FIGS. 4A–4B show the alignment of the deduced amino acid sequences of the three cloned NHE3 homologues. Human NHE3 is 89% identical at the amino acid level to rat NHE3 and 88% identical to rabbit NHE3.

The human NHE3 composite cDNA was stably transfected into NHE deficient cell line, PS120, a NHE deficient derivative of the Chinese hamster lung fibroblast cell line CCL39 by $CaPO_4$ precipitation. Transfection allowed these cells to perform $Na^+/H^+$ exchange, assessed by $Na^+$ dependent alkalinization and measured by the fluorescence of the acetoxymethyl ester of 2', 7'-bis(2-carboxyethyl)-5-(and-6) carboxyfluorescein (BCECF).

Human brush border epithelial $Na^+/H^+$ exchange has been characterized as being much less sensitive to inhibition by amiloride and its 5-amino-substituted analogues than basolateral and nonepithelial membrane $Na^+/H^+$ exchangers (10, 24,36). Thus, we assessed the sensitivity of human NHE3 to inhibition by amiloride and ethylisopropylamiloride (EIPA) by $^{22}Na^+$ uptake studies (FIG. 6). Our studies demonstrated that the sensitivity of human NHE3 is in the range of that of rabbit and rat NHE3 (Table 1) (19,29):

TABLE I

Effect of amiloride and ethylisopropylamiloride
on human, rabbit and rat NHE3
Inhibition constants ($IC_{50}$ in $\mu M$)

|  | Amiloride | Ethylisopropylamiloride |
| --- | --- | --- |
| Human NHE3 | 49 | 6.6 |
| Rat NHE3 | 100 | 2.4 |
| Rabbit NHE3 | 39 | 8.0 |

In regards to amiloride and EIPA sensitivity, we note that the amino acid sequence of FFFYL in putative MSD 4, previously shown by Counillon et al. and Yun et al. to be a critical region in the determination of NHE amiloride and EIPA sensitivity (7,35), is entirely conserved among all three NHE3 homologues.

Also similar to rabbit and rat NHE3 (14,19,29), we found that human NHE3 was activated by FGF, an activator of a receptor tyrosine kinase, and was inhibited by PMA, an activator of protein kinase C FIGS. 7A–7B. In the region C-terminal of MSD 10, which is essential for protein kinase regulation (5,32), there are 8 potential protein kinase C consensus sequences conserved among all three cloned $Na^+/H^+$ exchangers and a single conserved tyrosine kinase site at human NHE3 amino acid 546 (FIGS. 4A–4B). Nonetheless, there was no effect of 8-bromo-cAMP on human NHE3/PS120 cells, in spite of the presence of putative cAMP dependent protein kinase consensus sequences in the C-terminus. This was not surprising as none of the cloned mammalian $Na^+/H^+$ exchangers transfected into PS120 cells have been shown to be affected by addition of cAMP (28), although the cloned trout $Na^+/H^+$ exchanger ($\beta$-NHE) is regulated by cAMP in PS120 cells (5).

Across species, the overall sensitivity of NHE3 to amiloride inhibition and its regulation by second messengers is conserved. The relative amiloride resistance of human NHE3, its inhibition by PMA, and its expression being greatest in the kidney and small intestine is consistent with human NHE3 being the characteristic brush border $Na^+/H^+$ exchanger of these tissues. Indeed, recent Western analysis and immunohistochemical studies of human ileum and ascending colon, stained with antibody made against the rabbit NHE3 C-terminus, have confirmed that human NHE3 is present on the brush border membranes but not the basolateral membranes of human ileal villus and ascending colonic surface $Na^+$ absorbing epithelial cells (9). NHE3 is therefore a likely candidate to be the $Na^+/H^+$ exchanger isoform altered in diseases of the kidney and small intestine in which brush border $Na^+/H^+$ exchange activity is abnormal.

In this regard, we note that the literature reports that there is increased $Na^+/H^+$ exchange in the brush border of intestinal cells of patients with cystic fibrosis and that this likely contributes to the manifestations of the disease with desiccated luminal contents (37). A potential therapy for cystic fibrosis may be the inhibition of brush border $Na^+/H^+$ exchange. If such therapy is to succeed, drugs that inhibit brush border $Na^+/H^+$ exchange must be identified and tested. In one embodiment, a cell stably transfected with human NHE3 cDNA could be used to screen such drugs. In a preferred embodiment, the cell is PS120. Given the present disclosure, those of ordinary skill in this art could set up a screen to assess the affect of drugs on brush border $Na^+/H^+$ exchangers. For example, one could measure $Na^+/H^+$ exchanger activity by assessing $Na^+$ dependent alkalinization using fluorescence measurement with BCECF as set forth in the Methods section. Alternatively, one could measure $^{22}Na^+$ uptake, also as set forth in the Methods section.

Such screens may also be used for assessing drugs for the treatment of diarrhea. In virtually all diarrheal diseases, there is inhibition of brush border $Na^+/H^+$ exchange in the small bowel or colon (38). Accordingly, drugs that stimulate NHE3 may well be useful for the treatment of acute and chronic diarrhea, and the screens described above may be used to assess a drug's ability to stimulate NHE3. This methodology, in summary, could be used as a screen to assess the affect of drugs for conditions where either NHE3 may be malfunctioning and/or the modification of NHE3's native $Na^+/H^+$ exchange activity may have a potential therapeutic benefit.

Human NHE3, like rabbit NHE1, rabbit NHE2 and rabbit NHE3, exhibited evidence of a $H^+$ modifier site, with Hill coefficients of 2 (14). As we have noted previously, this contradicts some vesicle transport studies claiming that ileal brush border and basolateral, and colonic brush border membranes $Na^+/H^+$ exchangers have non-allosteric, Michaelis-Menten relationships between $[H^+]$ concentration and $Na^+/H^+$ exchange rate (27). The affinity of human NHE3 for $H^+$ (K') was likewise similar to that reported for rabbit NHE2 and NHE3 (14).

Unlike NHE3 in the rat and rabbit, we found that human NHE3 message is expressed in a variety of both epithelial and nonepithelial tissues. NHE3 in the rat and rabbit has not been detected in any tissues outside the kidney and the gastrointestinal tract, with the exception of one recent study by Bookstein, et al. reporting faint message detection in the rat brain (3,20,26). NHE3 expression has not been examined in the rat or rabbit ovary, prostate, thymus, leukocyte, or placenta (20,26). Orlowski et al. detected no NHE3 message in the rat testes or spleen, in contrast to our finding of relatively abundant NHE3 message in the human testes, and relatively low message in the human spleen. In the human, therefore, NHE3 most likely has significant roles in other tissues, for which the transepithelial absorption of $Na^+$ is not thought of as a primary physiologic function.

The relative degree of expression of human NHE3 in kidney and gut tissues is similar to that found for the rabbit (26), although human NHE3 expression in the colon was much less than in the small intestine whereas rabbit NHE3 expression in the ascending colon was equal to that found in the ileum. Some of these differences may be attributed to sampling differences, as the human colon mRNA studied was derived from both the ascending and transverse colon. Interestingly, message expression of human NHE3 for the kidney and gut is opposite that found in the rat, in which two studies report message expression in the following order: colon>small intestine>kidney (3,20). It is noteworthy that in the human, NHE3 message of two sizes (6.7 and 8.9 kb) is expressed nearly equivalently in all tissues except the kidney and gut. In these latter two organs, expression was almost completely limited to the 6.7 kb band.

We provide the following specific methods that may be used in the practice of the claimed invention. It is to be understood that both the foregoing general description and the following detailed description are exemplary and explanatory only and are not restrictive of the invention as claimed.

Methods

In conducting the experiments described in the Examples below, we used the following methods:

cDNA Library Screening

The human NHE3 partial cDNA clone, HKC-3, was used to rescreen, under conditions of high stringency (hybridized at 42° C. in 50% formamide, 4×SSC, 5×Denhardt, 1% sodium dodecyl sulfate (SDS) and washed at 62° C. in 0.15×SSC and 0.1% SDS) the same human kidney cortex λgt10 cDNA library from which it was isolated (obtained from Dr. G. I. Bell, the University of Chicago). Six positive clones were identified, and their cDNA inserts were subcloned into plasmid pBluescript II KS (Stratagene) and sequenced on both ends. One of these clones, HKC-5, was further characterized (FIG. 1).

RT-PCR Cloning

To obtain 5' human NHE3 sequence, 1 $\mu$g of human kidney RNA, obtained from Dr. Pat Wilson (The Johns Hopkins Univ.), was reverse transcribed (RT), using random primers into cDNA using the SuperScript Preamplification System for First Strand cDNA Synthesis kit (GIBCO) according to the manufacturer's recommendations. 2 $\mu$l of RT product was used as template in a 50 $\mu$l polymerase chain reaction (PCR) (39) containing (final amounts/concentrations) 10× PCR II buffer (5 $\mu$l), deoxynucleotides (300 $\mu$M), formamide (3%), Taq polymerase (Perkin Elmer Cetus) (2 U), reverse HKC-3 primer B3 (5'-GCGAATTCCACACGGTACCCACGAC-3') (30 pmol) (SEQ ID NO:1) and degenerate NHE3 minicistron forward primer B8 5'-ATGCG (G/A/T/C)GT CGG(G/A/T/C) (C/T)CC (C/T)GG (C/A)GC TGAGC-3' (30 pmol) (SEQ ID NO:2) was based on the conserved minicistrons of rabbit and rat NHE3 (FIG. 2) (20,26). Amplification was performed for 30 cycles: 94° C. (75 s), 59° C. (45 s), and 72° C. (2 min). PCR product was separated on a 1.4% agarose gel and blotted onto nylon filters (Hybond). Filters were probed under high stringency conditions with a rabbit 5' NHE3 partial cDNA, clone RAI1 (26), to analyze for homologous 5' human NHE3 PCR product. Hybridizing RT-PCR clone 23-3 was subcloned into plasmid pCR II using the TA Cloning Kit (Invitrogen) and sequenced (FIG. 1).

cDNA Sequencing

Sequencing of the coding region of human NHE3 cDNA clones was performed on both strands by Sanger's dideoxy termination procedure using the Sequenase kit (USB Corp) (22). ExoIII/mung bean nuclease digestion was used to obtain progressive unidirectional deletion clones (26). Two regions of high GC content containing compression artifact (RT-PCR clone 23-3 and between nucleotides 2333 to 2571) were also sequenced using internal primers and the fluorescent dideoxy terminator method of cycle sequencing on an Applied Biosystems (Foster City, Calif.) 373a automated DNA sequencer, following ABI protocols at the DNA Analysis Facility of Johns Hopkins University (17,25).

Construction of a Full Length Human NHE3 Na+/H+ Exchanger Composite cDNA

Three overlapping clones, RT-PCR clone 23-3 and the human kidney cortex cDNA clones HKC-3 and HKC-5, produced the entire coding sequence of human NHE3 (FIG. 1). A 554 bp overlapping human NHE3 fragment (RT-PCR clone 25-1) was amplified to facilitate joining HKC-3 and HKC-5, and thereby enable construction of a human NHE3 expression construct: human kidney RNA was reverse transcribed as above and PCR amplification, using standard techniques, was performed using human NHE3 specific primers, forward primer B13 (5'-CATCTGGACCTGGAACACG-3') (SEQ ID NO:3) reverse primer B14 (5'-CGTAGCTGATGGCATCCTTC-3')(SEQ ID NO:4). The identity of RT-PCR clone 25-1 was confirmed by sequencing. To create a composite NHE3 full-length coding cDNA, clones 25-1, HKC-5, HKC-3 and 23-3 were subcloned into a pUC 19 vector using the restriction sites as noted in FIG. 1 and standard restriction digestion and ligation techniques. The NHE3 composite cDNA construct contained 10 bp of 5' untranslated NHE3 cDNA, the entire coding region of human NHE-3 and 2.2 kb of 3' untranslated cDNA sequence (FIG. 1, human NHE3 expression construct). This was subcloned directionally into the EcoRI/XbaI sites of the eukaryotic expression vector PECE (35) to create human NHE3 expression plasmid, pEH3.

Stable Expression of the Human NHE3 Composite cDNA in Na+/H+ Exchange Deficient Fibroblasts The pEH3 construct was stably cotransfected with pSV2neo (Clontech) into the Na+/H+ exchanger deficient cell line PS120, a Na+/H+ exchanger deficient derivative of the Chinese hamster lung fibroblast cell line CCL39, by the method of CaPO$_4$ precipitation as described previously (23). Transfected cells (HNHE3/PS120 cells) were selected by both G418 resistance and the acid loading technique (23,30).

Measurement of Na+/H+ Exchange Activity: Fluorescence Measurement with BCECF HNHE3/PS120 cells were grown to 70–80% confluency on glass coverslips, serum starved overnight to arrest growth, washed with Na+ medium (containing in mM: 130 NaCl, 5 KCl, 2 CaCl$_2$, 1 MgSO$_4$, 1 NaPO$_4$, 25 glucose, 20 HEPES, pH 7.4) and loaded with the acetoxymethyl ester of 2',7'-bis(2-carboxyethyl)-5-(and-6)carboxyfluorescein (BCECF) as previously discussed (31). Cells were washed with TMA medium (containing in mM: 130 tetramethylammonium-Cl, 5 KCl, 2 CaCl$_2$ 1 MgSO$_4$, 1 TMA-PO$_4$, 25 glucose, 20 HEPES, pH 7.4), mounted in a cuvette, and perfused at 37° C. Cells were acidified by perfusing with 30 mM NH$_4$Cl prepulse followed by removal of NH$_4$Cl with TMA medium. The cuvette was then perfused with Na+ medium. Na+ dependent alkalinization, which was amiloride sensitive, as determined by BCECF fluorescence, was measured in an SLM spectrofluorometer as described (31). Na+/H+ exchange was determined by multiplying the initial rate of Na+ dependent alkalinization by intracellular buffering capacity, as described.

To determine the Hill coefficient n and the apparent H+ affinity constant K', a kinetic measure of H+ exchange (1), we obtained a plot of intracellular [H+] concentration versus rate of proton efflux by calculating the first-order derivative of the Na+-dependent pH recovery curve X intracellular buffering capacity, as previously described (14). Data points generated from 8 coverslips were recorded at 3 s intervals during the rapid phase of pH recovery, with longer (15 s) intervals between data points as the rate of alkalinization slowed. Data were analyzed using a nonlinear regression data analysis program (ENZFITTER, Biosoft Corp.).

$^{22}$Na+ Uptake Studies

Stably transfected HNHE3/PS 120 cells were grown to near confluency in 24-well plates. The cells were serum-starved for 24 hours to arrest growth. $^{22}$Na+ uptake (1 mM) was measured during the linear phase of uptake in the presence of 1 mM ouabain and various concentrations of potential inhibitors amiloride or ethylisopropylamiloride (EIPA) following acidification with NH$_4$Cl prepulse, as detailed previously (30).

Northern Blot Analysis and RT-PCR Confirmation of Results

Commercially available human Northern blots, human MTN and human MTN II (Clontech), each containing poly(A)+ RNA, 1 μg per lane, from 8 different human tissue types, were probed with the 953 bp 5' SmaI fragment of clone HKC-5 (see FIG. 1) encoding amino acids 462 through 775, according to the manufacturer's instructions for high stringency probing. $2 \times 10^6$ cpm of randomly primed, $^{32}$P-labelled probe was added to each ml of hybridization solution. Blots were analyzed by autoradiography using Kodak XAR film.

EXAMPLE 1

Cloning and Sequencing of a Composite cDNA Encoding Human NHE3

To extend the human NHE3 cDNA beyond that of the previously reported human NHE3 partial cDNA clone, HKC-3, we reprobed the human kidney cortex library using HKC-3 as a probe and identified an additional NHE3 clone, HKC-5 (FIG. 1). Clone HKC-5 overlapped with clone HKC-3 and contained the entire 3' coding and noncoding region of human NHE3, including the poly(A)+ tail. It has been surprisingly found that, despite extensive efforts to utilize colony hybridization library screening of the same lamda gt10 human kidney from which HKC-3 was isolated, we were unable to isolate the complete 5' coding nucleotides of the NHE3 full length cDNA.

The most 5' clone isolated was HKC-10, which encoded human NHE3 cDNA 182 nucleotides 5' of clone HKC-3, at putative membrane spanning domain 2 as based on homology with the rabbit NHE3. Interestingly, the most 5' nucleotide sequence of clone HKC-10 was at a location homologous to the most 5' nucleotides of exon 2 of human NHE1. It is known that a 41.5 Kb intron separates exons 1 and 2 in human NHE1 (44). We have very recently obtained a human NHE3 genomic DNA cosmid clone, clone 84C11, and have found that, as in NHE1, an intron/exon boundary is likewise present in NHE3 immediately 5' to clone HKC-10. Furthermore, this cosmid clone does not contain human NHE3 putative exon 1, suggesting that the human NHE3 exon 1 is most likely separated from exon 2 by a relatively large intron, as found in NHE1. It may be that a large intron segment between exons 1 and 2 may have made obtaining NHE3 cDNA clones encoding exon 1 difficult.

Additionally, as we later determined, there ultimately was found to be a segment in the 5' coding region of NHE3, between coding nucleotides 12 to 107 (FIG. 3) which was 87% GC rich. As noted below, this high GC rich region also was found to make the molecular cloning and sequencing of the 5' region of NHE3 difficult, and required a modification of the usual methodology.

We also screened three cDNA libraries, this same human kidney cortex lamda gt10 library and both human jejunal lamda gt11 and a human fetal kidney lamda gt10 libraries, by a polymerase chain reaction method of library screening using a modification of the method described by Tung et al. and using NHE3 specific antisense primers derived from HKC-3 and HKC-10 sequence (43). Additional 5' human NHE3 clones were identified from these other libraries but no clones contained the entire remaining 5' coding nucleotides of NHE3. Therefore, after screening three libraries that had NHE3 5' clones but not the entire 5' coding segment, we embarked on a new method to clone this region.

A degenerate forward primer B8, was developed from the sequences encoding minicistrons found in the 5' untranslated regions of both rabbit and rat NHE3 (FIG. 2; Nucleotide identity is designated by "*"). (20,26). We ultimately obtained the remaining 5' coding region, by reverse transcription/polymerase chain reaction (RT-PCR) of human kidney RNA, based on a reverse primer B3, derived from HKC-3, and the forward primer B8. The RT-PCR amplification yielded a 500 bp PCR product, clone 23-3 , that had high homology with the 5' coding region of rabbit NHE3. Its sequence contained the remaining 5' coding sequences of human NHE3 and ten 5' noncoding nucleotides, between the minicistron primer sequence and the putative ATG start site.

Due to the high GC rich segment in this region as noted above (the region from bp 12 to 107 has 87% GC content), the polymerase chain reaction amplification of this region required using 3% formamide as a denaturant. Similarly, this region could not be sequenced correctly using Sanger's dideoxy termination procedure (22). Rather, it required amplifying the region using the polymerase chain reaction with addition of 200 μM 7-dcaza-dGTP (to weaken the GC hydrogen bonds that interfere with polymerization fidelity) and 100 μM dGTP in place of 300 μM dGTP nucleotide alone, then electroeluting the amplified PCR product. The electroeluted PCR product was directly sequencing by using internal primers and the fluorescent dideoxy terminator method of cycle sequencing on an Applied Biosystems (Foster City, Calif.) 373a automated DNA sequencer, following ABI protocols at the DNA Analysis facility of Johns Hopkins University (17, 25).

FIG. 1 shows a schematic diagram of the human NHE3 composite cDNA. The open reading frame is represented by the hatched area and the noncoding regions by the open bars. Nucleotide numbers are indicated on the top of the clones. Primers (B3, B8, B13, and B14) used to amplify NHE3 RT-PCR clones are represented by shaded bars. Each primer's name is listed below and separated by an arrow from its corresponding bar. Restriction enzyme sites used in constructing a composite human NHE3 cDNA or used in constructing a human NHE3 cDNA probe (i.e. SmaI) are indicated by the vertical lines intersecting the clones. The human NHE3 cDNA construct used in the expression studies is represented by the solid horizontal bar ("Human NHE3 Expression Construct"). The partial cDNA clones used to produce this construct are designated underneath this bar. They are separated by vertical lines representing the points of their restriction digestion and ligation.

The nucleotide and amino acid sequences of human NHE3 are presented in FIG. 3A–3B. Nucleotides are numbered at the right of the sequence with respect to their putative translation initiation site. Amino acids are numbered at the left of the sequence and are represented by their single letter abbreviations. "*" represents an in-frame stop codon.

This nucleotide sequence shares 82% identity with rat NHE3 and 81% identity with rabbit NHE3 (20,26). The largest open reading frame, a series of codons coding for amino acids which is translatable into a protein, is 2502 bp, 9 bp larger than that of rat NHE3 and 6 bp larger than that of rabbit NHE3. The initiation codon is in fair agreement with Kozak's consensus sequence, having a G at bp −3 but a T at bp +4 (13). The next in-frame initiation codon is at MSD 4. Based on the size of clone HKC-5, the 3' untranslated region of NHE3 is roughly 3 kb, of which the most 5-prime 72 bp and the 3' polyadenylation sequence have been determined. There was 74% identity between the first 39 bp 3' untranslated nucleotides of human and rat NHE3. Homology 3' of this region between human and rat NHE3 is insignificant. Only the first 38 bp 3' noncoding nucleotides of rabbit NHE3 have been identified (26); these have 92% identity with human NHE3.

The deduced amino acid sequence, based on the identity of the three-nucleotide codon, of human NHE3 is 834 residues. The calculated relative molecular weight is 92,906.

FIGS. 4A–4B shows the alignment of the deduced amino acid sequence of the three cloned NHE3 homologues. Rat NHE3 sequence was obtained from Orlowski et al. and rabbit NHE3 from Tse et al. (20,26). Amino acids are indicated by their single letter abbreviation. Membrane spanning domains are overlined (m1–m10, m5a, and m5b) and were used as previously determined for rabbit NHE3 (26). Eight conserved putative protein kinase C phosphorylation consensus sequences are indicated by "#" overlying the serine or threonine residue. A single conserved tyrosine kinase phosphorylation consensus sequence is indicated by "+". Identical amino acids are indicated by "*", and "." indicates similarity. Amino acid numbers are shown on the right.

The three cloned NHE3 homologues are overall 82% identical; human NHE3 is 89% identical at the amino acid level to rat NHE3 and 88% identical to rabbit NHE3. As found for the NHE1 homologues (20,23,31), amino acid homology across species for NHE3 is greatest in the region between MSD 2–10; human NHE3 and rat NHE3 are 94% identical in this region as is human NHE3 and rabbit NHE3. The NHE3 proteins, again like the NHE1 proteins, diverge most near their N-termini; human and rabbit NHE3 identity is 62% N-terminal of MSD 2, and human and rat NHE3 identity is 49%. The cytoplasmic tails of the NHE3 proteins are highly conserved, 88% identity for human and rabbit NHE3 and 89% identity for human and rat NHE3. A single N-linked glycosylation consensus sequence is present at human NHE3 amino acid 326, and is conserved among all mammalian $Na^+/H^+$ exchanger isoforms (28).

EXAMPLE 2

Functional Characterization of Human NHE3 cDNA in $Na^+/H^+$ Exchanger Deficient Fibroblasts To characterize the kinetic properties of human NHE3, we created a composite human NHE3 cDNA from the four human NHE3 partial cDNA clones diagrammed in FIG. 1. This composite cDNA contained the minicistron primer B8 sequence at its 5' most end, the 10 intervening 5' untranslated nucleotides, the entire coding sequence and 2.2 kb of the 2.9 kb 3' untranslated sequence. This cDNA was subcloned into the expression vector pECE, then stably transfected into the $Na^+/H^+$ exchanger deficient cell line PS120. The stably transfected human NHE3/PS120 cells (HNHE3/PS120), following acidification, showed rapid alkalinization upon addition of 130 mM $Na^+$ (FIG. 5A).

FIG. 5A sets forth a composite tracing of two representative experiments demonstrating $pH_i$ recovery of PS120 cells stably transfected with the human NHE3 expression vector pEH3. HNHE3/PS120 cells loaded with BCECF were acidified by $NH_4Cl$ prepulse. In the presence of 130 mM $Na^+$ medium (curve A), but not 130 mM TMA medium, cells were able to recover to a steady-state $pH_i$. Addition of 1 mM amiloride in the presence of 130 mM $Na^+$ medium inhibits this recovery (curve B), proving that cloned human NHE3 is an amiloride inhibitable $Na^+/H^+$ exchanger.

FIG. 5B demonstrates that the $Na^+/H^+$ exchange activity of HNHE3/PS120 cells with respect to intracellular $[H^+]$ concentration fits a sigmoidal rather than hyperbolic curve, demonstrating cooperative allosteric kinetics: Hill coefficient ($n_{app}$) was 2.0 and the apparent $H^+$ affinity constant K' was 0.164 $\mu$M. Specifically, we conducted a kinetic analysis of HNHE3/PS120 cells, expressed as $H^+$ efflux rate, as a function of intracellular $[H^+]$ concentration. HNHE3/PS120 cells were plated on eight glass coverslips and serum starved overnight. Initial rates of $pH_i$ recovery were obtained by calculating the first-order derivative of eight $pH_i$ recovery traces, a single trace as shown in FIG. 5A. $Na^+/H^+$ exchange rates ($\mu$M $H^+$ per s)(□) were determined as described in Methods. The line in the plot was generated by the computer program using the Hill equation and was the best fit with the data. As noted above, the Hill coefficient ($n_{app}$) was 2.0; the apparent $H^+$ affinity constant K' was 0.164 $\mu$M and $V_{max}$ was 2400 $\mu$M/sec.

Human brush border epithelial $Na^+/H^+$ exchange has been characterized as being much less sensitive to inhibition by amiloride and its 5-amino-substituted analogues than basolateral and nonepithelial membrane $Na^+/H^+$ exchangers (10, 24,36). Therefore we determined the quantitative sensitivity of HNHE3/PS120 cells to inhibition by amiloride and EIPA by $^{22}Na^+$ uptake studies. The concentration dependence for amiloride and EIPA inhibition of the initial rate of $^{22}Na^+$ uptake (1 mM) into acid loaded HNHE3/PS120 cells was determined.

Three independent experiments were performed. The mean $IC_{50}$ values for amiloride and EIPA were 49.0 $\mu$M and 6.6 $\mu$M, respectively. FIG. 6 provides curves are from a representative experiment. Each point represents the mean percent of control $^{22}Na^+$ uptake of duplicate experiments for each concentration of inhibitor. The curves are nonlinear least squares fits of the data assuming a single binding site for the inhibition (GraphPAD Software, Inc., San Diego, Calif.). The $IC_{50}$ values for these representative curves were calculated to be 59 and 8.8 $\mu$M for amiloride and EIPA, respectively.

To determine second messenger regulation of human NHE3, we studied the effects of fibroblast growth factor (FGF), the cAMP analogue 8-bromo-cAMP, and phorbol 12-myristate 13-acetate (PMA). Serum starved HNHE3/PS120 cells were acidified by a $NH_4Cl$ prepulse and allowed to recover in 130 mM $Na^+$ medium until steady-state $pH_i$ was obtained. Either FGF (10 ng/ml), 8-bromo-cAMP (0.5 mM) or PMA (1.0 $\mu$M) was then added at the times indicated in FIGS. 7A–7B. In comparison to controls, addition of FGF caused activation of the HNHE3/PS120 cells, which reached a new steady state after an average of 5 min (FIG. 7A); $\Delta pH_i$ was +0.051±0.016 following addition of FGF versus −0.006±0.012 for controls followed over a similar time period (p<0.035, n=4). Addition of 8-bromo-cAMP at steady state had no measurable effect on $Na^+/H^+$ exchange activity (n=2). PMA, in contrast, resulted in a fall of the $pH_i$ from its steady-state value, reaching a new steady state after an average of less than 2 min: $\Delta$pH. was −0.052±0.006 (p<0.001, n=5) (FIG. 7B). This signifies inhibition of the transfected $Na^+/H^+$ exchanger. We have previously demonstrated that PMA does not cause acidification in PS120 cells outside of its inhibition of the $Na^+/H^+$ exchanger (29).

EXAMPLE 3

Northern Blot Analysis and Tissue Distribution of Human NHE3 Message

To determine the size of the human NHE3 message and to examine its expression in a variety of human tissues, we probed Northern blots of multiple human tissues (commercially prepared human Northern blots, Human MTN and Human MTN II, Clontech) with the 935 bp 5' SmaI fragment of clone HKC-5 (FIG. 8).

Each lane contained 1 μg of poly(A)+ RNA from the indicated tissues. Both blots (left panel=MTN blot, right panel=MTN blot II) were probed in a single solution under high stringency conditions using the human NHE3 specific $^{32}$P probe. The blots were washed together under high stringency conditions. Autoradiograms were exposed for two different time periods: A, 16 h; B, 7 days. RNA size standards (in kilobases) are shown on the right of the figures.

We used the cytoplasmic domain probe because homology in this region among NHE isoforms is low (47% nucleotide identity with NHE2, 41% with NHE1), minimizing possible cross hybridization with other NHE isoforms. Furthermore, we confirmed that this NHE3 probe did not hybridize to NHE1 or NHE2 by Southern blotting under high stringency hybridization conditions (data not shown).

At 16 h exposure of the autoradiogram (FIG. 8, panel A), a strong 6.7 kb band was detected in human kidney RNA, and a weaker 6.7 kb band was detected in the small intestine RNA, with two very weak bands detected in testes RNA, corresponding to 6.7 and 8.9 kb. Following a 7 day exposure, bands were detected in RNA from all tissues from the MTN II blot, and two additional tissues (brain and placenta) in the MTN blot (FIG. 8, panel B). The order of signal intensity for the various tissues was: kidney>>small intestine>>testes>ovary>colon=prostate>thymus >peripheral leukocyte=brain>spleen>placenta, and including endothelial cells. No message was detected in the heart, lung, liver, skeletal muscle, or pancreas. The bands in the kidney, small intestine and colon appeared to be made up almost entirely of the 6.7 kb size, whereas the 8.9 kb band seen in the other tissues were nearly as intense as the 6.7 kb band.

As NHE3 message in the rabbit and rat has only been detected in kidney, stomach, some intestinal tissues and brain (3,20,26), the finding that human NHE3 was present in these other tissues was unexpected. Consequently, we probed a newly obtained second MTN II blot, and the results from the first MTN II blot were confirmed. Furthermore, both MTN II blots were stripped and reprobed with a mouse protamine-1 cDNA (ATCC, Rockville, Md.) (33). The only hybridization signal present was that of the testicular specific 0.6 kb human protamine-1 message (8), seen only in the testes lanes, thus verifying the integrity and specificity of the MTN II blots' testes samples (results not shown).

REFERENCES

1. Aronson, P. S. Mechanisms of active H+ secretion in the proximal tubule. *Am. J. Physiol.* 245: F647–F659, 1983.

2. Biemesderfer, D., J. Pizzonia, A. Abu-Alfa, M. Exner, R. Reilly, P. Igarashi, and P. S. Aronson. NHE3: a Na+/H+ exchanger isoform of renal brush border. *Am. J. Physiol.* F736–F742, 1993.

3. Bookstein, C., A. M. DePaoli, Y. Xie, P. Niu, M. W. Musch, M. C. Rao, and E. B. Chang. Na+/H+ exchangers, NHE-1 and NHE-3, of rat intestine: expression and localization. *J. Clin. Invest.* 93: 106–113, 1994.

4. Booth, I. W., G. Stange, H. Murer, T. R. Fenton, and P. J. Milla. Defective jejunal brush-border Na+/H+ exchange: A cause of congenital secretory diarrhoea. *Lancet* i: 1066–1069, 1985.

5. Borgese, F., C. Sardet, M. Cappadoro, J. Pouyssegur, and R. Motais. Cloning and expressing a cAMP-activated Na+/H+ exchanger: evidence that the cytoplasmic domain mediates hormonal regulation. *Proc. Natl. Acad. Sci. USA* 89: 6765–6769, 1992.

6. Brant, S. R., M. Bernstein, J. J. Wasmuth, B. W. Taylor, J. D. McPherson, X. Li, S. Walker, J. Pouyssegur, M. Donowitz, C. M. Tse, and E. W. Jabs. Physical and genetic mapping of a human apical epithelial Na+/H+ exchanger (NHE3) isoform to chromosome 5p15.3. *Genomics* 15: 668–672, 1993.

7. Counillon, L., A. Franchi, J. Pouyssegur. A point mutation of the Na+/H+ exchanger gene (NHE-1) and amplification of the mutated allele confer amiloride-resistance upon chronic acidosis. *Proc. Natl. Acad. Sci. USA* 90: 4508–4512, 1993.

8. Domenjoud, L., H. Kremling, P. Burfeind, W. M. Maier, and W. Engel. On the expression of protamine genes in the testis of man and other mammals. *Andrologia* 23: 333–337, 1991.

9. Hoogerwerf, W. A., C. Yun, S. Levine, J. L. M. Montgomery, A. J. Lazenby, C. M. Tse and M. Donowitz. Message distribution of three Na/H+ exchangers along the rabbit ileal crypt-villus axis and demonstration that an epithelial isoform, NHE2, is present in ileal brush border membrane. *Gastroenterology* 106: A239 (Abstract), 1994.

10. Kleihnman, J. G., J. M. Harig, J. A. Barry, K. Ramaswamy. Na+ and H+ transport in human jejunal brushborder membrane vesicles. *Am. J. Physiol.* 255: G206–G211, 1988.

11. Knickelbein, R. G., P. S. Aronson, W. Atherton, and J. W. Dobbins. Na and Cl transport across rabbit ileal brush border. I. Evidence for Na/H exchange. *Am. J. Physiol.* 245: G504–G510, 1983.

12. Knickelbein, R. G., P. S. Aronson, J. Seifter, C. M. Schron and J. W. Dobbins. Na and Cl transport across rabbit ileal brush border. II. Demonstration of Cl/HCO$_3$ exchange and mechanism for coupling. *Am. J. Physiol.* 249: G236–G249, 1985.

13. Kozak, M. An analysis of 5'-noncoding sequences from 699 vertebrate messenger RNAs. *Nucleic Acids Res.* 15: 8125–8148, 1987.

14. Levine, S., M. Montrose, C. M. Tse, and M. Donowitz. Kinetics and regulation of three cloned mammalian Na+/H+ exchangers stably expressed in a fibroblast cell line. *J. Biol. Chem.* 268: 25527–25535, 1993.

15. Lifton, R. P., C. Sardet, J. Pouyssegur, and J. M. Lalouel. Cloning of the human genomic amiloride-sensitive Na+/H+ antiporter gene, identification of genetic polymorphisms, and localization on the genetic map of chromosome 1p. *Genomics* 7:131–135, 1990.

16. Mahnensmith, R. L. and P. S. Aronson. The plasma membrane sodium-hydrogen exchanger and its role in physiological and pathophysiological processes. *Circ. Res.* 56:773–788, 1985.

17. McCombie, W. R., C. Heiner, J. M. Kelly, M. G. Fitzgerald, and J. D. Gocayne. Rapid and reliable fluorescent cycle sequencing of double stranded templates. *DNA Sequence* 2: 289–296, 1992.

18. Morduchowicz, G. A., D. Sheikh-Hamad, O. D. Jo, E. P. Nord, D. B. Lee, and N. Yanagawa. Increased Na+/H+ antiport activity in the renal brush border membrane of SHR. *Kidney Int.* 36:576–581, 1989.

19. Orlowski, J. Heterologous expression and functional properties of amiloride high affinity (NHE3) and low affinity (NHE3) isoforms of the rat Na+/H+ exchanger. *J. Biol. Chem.* 268: 16369–16377, 1993.

20. Orlowski, J., R. A. Kandasamy, and G. E. Shull. Molecular cloning of putative members of the Na+/H+ exchanger gene family. *J. Biol. Chem.* 267: 9331–9339, 1992.

21. Rood, R. P. and M. Donowitz. Regulation of small intestinal Na$^+$ absorption by protein kinases; implications for therapy of diarrheal diseases. *Viewpoints on Digestive Disease* 22: 1–6, 1990.

22. Sanger, F., S. Nicklen, and A. R. Coulson: DNA sequencing with chain-termination inhibitors. *Proc. Natl. Acad. USA* 74: 5463–5467, 1977.

23. Sardet, C., L. Counillon, A. Franchi, and J. Pouyssegur. Molecular cloning, primary structure and expression of the human growth factor-activatable Na$^+$/H$^+$ antiporter. *Cell* 56: 271–280, 1989.

24. Simchourtz, L., and E. J. Cragoe. Intracellular acidification-induced alkali metal cation He exchange in human neutrophils. *J. Gen. Physiol.* 90: 737–762, 1987.

25. Smith, L. M., J. Z. Sanders, R. J. Kaiser, P. Hughes, C. Dodd, C. R. Connell, C. Heiner, S. B. H. Kent, and L. E. Hood: Fluorescence detection in automated DNA sequence analysis. *Nature* 321: 674–679, 1986.

26. Tse, C. M., S. R. Brant, S. Walker, J. Pouyssegur, and M. Donowitz. Cloning and sequencing of a rabbit cDNA encoding an intestinal and kidney-specific Na$^+$/H$^+$ exchanger isoform (NHE-3). *J. Biol. Chem.* 267: 9340–9346, 1992.

27. Tse, C. M., S. Levine, C. H. C. Yun, S. R. Brant, L. Counillon, J. Pouyssegur, and M. Donowitz. Structure/function studies of the epithelial isoforms of the mammalian Na$^+$/H$^+$ exchanger gene family. *J. Membrane Biol.* 135: 93–108, 1993.

28. Tse, C. M., S. Levine, C. H. C. Yun, S. R. Brant, S. Nath, J. Pouyssegur, and M. Donowitz. Molecular properties, kinetics and regulation of mammalian Na$^+$/H$^+$ exchangers. *Cell Physiol. Biochem.* 4: 282–300, 1994.

29. Tse, C. M., S. A. Levine, C. H. C. Yun, S. R. Brant, J. Pouyssegur, M. H. Montrose, and M. Donowitz. Functional characteristics of a cloned epithelial Na$^+$/H$^+$ exchanger (NHE3): Resistance to amiloride and inhibition by protein kinase C. *Proc. Nat. Acad. Sci. USA* 90: 9110–9114, 1993.

30. Tse, C. M., S. A. Levine, C. H. C. Yun, M. H. Montrose, P. J. Little, J. Pouyssegur, and M. Donowitz. Cloning and expression of a rabbit cDNA encoding a serum-activated ethylisoprnpylamiloride-resistant epithelial Na$^+$/H$^+$ exchanger isoform (NHE-2). *J. Biol. Chem.* 268: 11917–11924, 1993.

31. Tse, C. M., A. I. Ma, V. W. Yang, A. J. M. Watson, S. Levine M. H. Montrose, J. Potter, C. Sardet, J. Pouyssegur, and M. Donowitz. Molecular cloning and expression of a cDNA encoding the rabbit ileal villus cell basolateral membrane Na$^+$/H$^+$ exchanger. *EMBO J.* 10: 1957–1967, 1991.

32. Wakabayashi, S., P. Fafournoux, C. Sardet, and J. Pouyssegur: The Na$^+$/H$^+$ antiporter cytoplasmic domain mediates growth factor signals and controls H$^+$-sensing. *Proc. Natl. Acad. Sci. USA* 89: 2424–2428, 1992.

33. Yelick, P. C., R. Balhorn, P. A. Johnson, M. C. Corzett, J. A. Mazrimas, K. C. Kleene, and N. B. Hecht. Mouse protamine 2 is synthesized as a precursor whereas mouse protamine 1 is not. *Mol. Cell Biol.* 7: 2173–2179, 1987.

34. Yun, C. H., S. Gurubhagavatula, S. A. Levine, J. M. Montgomery, S. R. Brant, M. E. Cohen, J. Pouyssegur, C. M. Tse, and M. Donowitz. Glucocorticoid stimulation of ileal Na$^+$ absorptive cell brush border Na$^+$/H$^+$ exchange and association with an increase in message for NHE-3, an epithelial isoform Na$^+$/H$^+$ exchanger. *J. Biol. Chem.* 268:206–211, 1993.

35. Yun, C. H. C., P. J. Little, S. K. Nath, S. A. Levine, J. Pouyssegur, C. M. Tse and M. Donowitz. Leu143 in the putative fourth membrane spanning domain is critical for amiloride inhibition of an epithelial Na$^+$/H$^+$ exchanger isoform (NHE2) *Biochem. Biophys. Res. Comm.* 193: 532–539, 1993.

36. Zamir, Z., J. A. Barry, and K. Ramaswamy. Sodium transport in human intestinal basolateral membrane vesicles. *Gastroenterology* 103: 1817–1822, 1992.

37. Berschneider, H. M, M. R. Knowles, R. G. Azizkhan, R. C. Boucher, N. A. Tobey, R. C. Orlando, and D. W. Powell. Altered intestinal chloride transport in cystic fibrosis. *FASEB J.* 2: 2625–2629, 1988.

38. Donowitz, M. and M. J. Welsh. Regulation of mammalian small intestinal electrolyte secretion. *Physiology of the Gastrointestinal Tract*, Ed. L. R. Johnson, Raven Press 2d ed. 1988, Chapter 48, 1351–1388.

39. U.S. Pat. Nos. 4,683,195 and 4,683,202.

40. Acra, S. and F. K. Ghisan. Increased Na$^+$/H$^+$ exchange in jejunal brush border membrane vesicles of spontaneously hypertensive rats. *Gastroenterology* 101: 430–436, 1991.

41. Freiberg J. M., J. Kinsella, and B. Sacktor. Glucocorticoids increase the Na$^+$/H$^+$ exchange and decrease the Na$^+$ gradient dependent phosphate uptake systems in renal brush border membrane vesicles. *Proc. Natl. Acad. Sci. USA* 79: 683–712, 1982.

42. Harguindey, S. and E. J. Cragoe Jr. The Na$^+$/H$^+$ antiporter in oncology in the light of the spontaneous regression of cancer and cell metabolism. *Medical Hypothesis* 39: 229–237, 1992.

43. Tung, J. S., B. L. Daugherty, L. O'Neill, S. W. Law, J. Han and G. E. Mark. PCR amplification of specific sequences from a cDNA library in *PCR Technology: Principles and Applications of DNA Amplification*. Erlich, H. A., Ed., Stockton Press, New York, 1989.

44. Miller, R. T., L. Counillon, G. Pages, R. P. Lifton, C. Sarget, and J. Pouyssegur. Structure of the 5'-flanking regulatory region in gene for human growth factor-activatable Na$^+$/H$^+$ exchanger NHE-1. *J. Bio. Chem.* 266: 10813–10819, 1991.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GCGAATTCCA CACGGTACCC ACGAC                                              25

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

ATGCGGTCGG CCGGGCTGAG C                                                  21

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

CATCTGGACC TGGAACACG                                                     19

(2) INFORMATION FOR SEQ ID NO:4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

CGTAGCTGAT GGCATCCTTC                                                    20

(2) INFORMATION FOR SEQ ID NO:5:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

ATGCGCGTCG GGCCCCGGCG CTGA                                          24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ATGCGTGTCG GCTCCTGGAG CTGA                                          24

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCAGGCGGCA                                                          10

(2) INFORMATION FOR SEQ ID NO:8:

(i) SEQUENCE CHARACTERISTICS:
        (A) LENGTH: 2574 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATGTGGGGAC TCGGGCCCG GGCCCCGAC CGGGGGCTGC TGCTGGCGCT G GCGCTGGGC      60

GGGCTGGCGC GGGCCGGGGG CGTCGAGGTG GAGCCCGGCG GCGCGCACGG C GAGAGCGGG   120

GGCTTCCAGG TGGTCACCTT CGAGTGGGCC CACGTGCAGG ATCCCTACGT C ATCGCGCTC   180

TGGATCCTCG TGGCCAGCTT GGCCAAGATC GGGTTCCACC TGTCCCACAA G GTCACCAGC   240

GTGGTTCCCG AGAGCGCCCT GCTCATCGTG CTGGGCCTGG TGCTGGGCGG C ATCGTCTGG   300

GCGGCCGACC ACATCGCGTC CTTCACACTG ACGCCCACCG TCTTCTTCTT C TACCTGCTG   360

CCCCCCATCG TGCTGGACGC CGGCTACTTC ATGCCCAACC GCCTCTTCTT C GGCAACCTG   420

GGGACCATCC TGTTGTACGC CGTCGTGGGT ACCGTGTGGA ACGCGGCCAC C ACCGGGCTG   480

TCCCTCTACG CGTCTTCCT CAGTGGGCTC ATGGGCGACC TGCAGATTGG G CTGCTGGAC   540

TTCCTCCTGT TTGGCAGCCT CATGGCGGCT GTGGACCCGG TGGCCGTCCT G GCCGTGTTT   600

GAGGAGGTCC ATGTCAACGA GGTCCTGTTC ATCATCGTCT TCGGGGAGTC G CTGCTGAAC   660

GACGCAGTCA CCGTGGTTCT GTACAATGTG TTTGAATCTT TCGTGGCGCT G GGAGGTGAC   720

AACGTGACTG GCGTGGACTG CGTGAAGGGC ATAGTGTCCT TCTTCGTGGT G AGCCTGGGG   780

GGCACGCTGG TGGGGTGGT CTTCGCCTTC CTGCTGTCGC TGGTGACGCG C TTCACCAAG   840

CATGTGCGTA TCATCGAGCC CGGCTTCGTG TTCATCATCT CCTACCTGTC C TACCTGACG   900

TCCGAGATGC TGTCGCTGTC GGCCATCCTC GCCATCACCT TCTGTGGCAT C TGCTGTCAG   960

AAGTATGTGA AGGCCAACAT CTCGGAGCAG TCGGCCACCA CCGTGCGCTA C ACCATGAAG  1020

```
ATGCTGGCCA GCAGCGCCGA GACCATCATC TTCATGTTCC TGGGTATCTC G GCCGTGAAC   1080

CCGTTCATCT GGACCTGGAA CACGGCCTTC GTGCTCCTGA CGCTGGTCTT C ATCTCCGTG   1140

TACCGGGCCA TCGGTGTGGT CCTGCAGACC TGGCTTCTGA ACCGCTACCG C ATGGTGCAG   1200

CTGGAGCCCA TTGACCAGGT GGTCCTGTCC TACGGGGGCC TGCGCGGGGC C GTGGCCTTT   1260

GCCCTGGTGG TGCTTCTGGA TGGAGACAAG GTCAAGGAGA GAACCTGTT C GTCAGCACC   1320

ACCATCATCG TAGTGTTGTT CACCGTCATC TTCCAGGGCC TGACCATCAA G CCTCTGGTG   1380

CAGTGGCTGA AGGTGAAGAG GAGCGAGCAC CGGGAACCTC GGCTCAACGA G AAGCTGCAC   1440

GGCCGCGCTT TCGACCACAT CCTCTCGGCC ATCGAGGACA TATCCGGACA G ATCGGGCAC   1500

AATTATCTCA GAGACAAGTG GTCCCACTTC GACAGGAAGT TCCTCAGCAG G GTCCTCATG   1560

AGACGGTCGG CCCAGAAGTC TCGAGACCGG ATCCTGAATG TCTTCCACGA G CTGAACCTG   1620

AAGGATGCCA TCAGCTACGT GGCTGAGGGA GAGCGCCGCG GGTCCCTGGC C TTCATCCGC   1680

TCCCCCAGCA CCGACAACGT GGTCAACGTG GACTTCACGC ACGATCGTC C ACCGTGGAG   1740

GCCTCTGTCT CCTACCTCCT GAGAGAAAAT GTCAGCGCTG TCTGCCTGGA C ATGCAGTCT   1800

CTGGAGCAGC GACGGCGGAG CATCCGGGAC GCGGAGGACA TGGTCACGCA C CACACGCTA   1860

CAGCAGTACC TGTACAAGCC GCGGCAGGAG TACAAGCATC TGTACAGCCG A CACGAGCTC   1920

ACGCCCACGG AGGACGAGAA ACAGGACCGG GAAATCTTCC ACAGGACCAT G CGGAAGCGC   1980

CTGGAGTCCT TCAAGTCGAC CAAGCTGGGG CTCAACCAGA CAAGAAGGC A GCCAAGCTG   2040

TACAAGCGGG AGCGTGCCCA GAAGCGGAGA AACAGCAGCA TCCCCAATGG G AAGCTGCCC   2100

ATGGAGAGCC CTGCGCAGAA TTTCACCATC AAGGAGAAAA ACTTGGAACT T TCAGACACC   2160

GAGGAGCCCC CCAACTATGA TGAGGAGATG AGTGGGGGGA TCGAGTTCCT G GCTAGTGTC   2220

ACCAAGGACA CAGCGTCCGA CTCCCCTGCA GGAATTGACA ACCCTGTGTT T TCTCCGGAC   2280

GAGGCCCTGG ACCGCAGCCT CCTGGCCAGG CTGCCGCCCT GGCTGTCTCC C GGGGAGACG   2340

GTGGTCCCCT CGCAGAGGGC CCGCACGCAG ATTCCCTACT CTCCCGGCAC C TTCCGCCGC   2400

CTGATGCCCT TCCGCCTCAG CAGCAAGTCC GTGGACTCCT TCCTGCAGGC A GACGGCCCC   2460

GAGGAGCGGC CCCCCGCCGC CCTCCCCGAG TCCACACACA TGTGACACCG G CTCCGACAC   2520

GCCGCTAACC GGCCGCTCGT CCCCGCGCCA CGGTCCGCCC ACCGCCGCCG C CGC        2574
```

(2) INFORMATION FOR SEQ ID NO:9:

(i) SEQUENCE CHARACTERISTICS:
        (A) LENGTH: 834 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Met Trp Gly Leu Gly Ala Arg Gly Pro Asp A rg Gly Leu Leu Ala
 1               5                  10                  15

Leu Ala Leu Gly Gly Leu Ala Arg Ala Gly G ly Val Glu Val Glu Pro
            20                  25                  30

Gly Gly Ala His Gly Glu Ser Gly Gly Phe G ln Val Val Thr Phe Glu
        35                  40                  45

Trp Ala His Val Gln Asp Pro Tyr Val Ile A la Leu Trp Ile Leu Val
    50                  55                  60

Ala Ser Leu Ala Lys Ile Gly Phe His Leu S er His Lys Val Thr Ser
```

```
                                -continued
65                    70                   75                   80
Val Val Pro Glu Ser Ala Leu Leu Ile Val L eu Gly Leu Val Leu Gly
                    85                  90                  95

Gly Ile Val Trp Ala Ala Asp His Ile Ala S er Phe Thr Leu Thr Pro
                100                 105                 110

Thr Val Phe Phe Phe Tyr Leu Leu Pro Pro I le Val Leu Asp Ala Gly
                115                 120                 125

Tyr Phe Met Pro Asn Arg Leu Phe Phe Gly A sn Leu Gly Thr Ile Leu
            130                 135                 140

Leu Tyr Ala Val Val Gly Thr Val Trp Asn A la Ala Thr Thr Gly Leu
145                 150                 155                 160

Ser Leu Tyr Gly Val Phe Leu Ser Gly Leu M et Gly Asp Leu Gln Ile
                165                 170                 175

Gly Leu Leu Asp Phe Leu Leu Phe Gly Ser L eu Met Ala Ala Val Asp
                180                 185                 190

Pro Val Ala Val Leu Ala Val Phe Glu Glu V al His Val Asn Glu Val
            195                 200                 205

Leu Phe Ile Ile Val Phe Gly Glu Ser Leu L eu Asn Asp Ala Val Thr
            210                 215                 220

Val Val Leu Tyr Asn Val Phe Glu Ser Phe V al Ala Leu Gly Gly Asp
225                 230                 235                 240

Asn Val Thr Gly Val Asp Cys Val Lys Gly I le Val Ser Phe Phe Val
                245                 250                 255

Val Ser Leu Gly Gly Thr Leu Val Gly Val V al Phe Ala Phe Leu Leu
                260                 265                 270

Ser Leu Val Thr Arg Phe Thr Lys His Val A rg Ile Ile Glu Pro Gly
                275                 280                 285

Phe Val Phe Ile Ile Ser Tyr Leu Ser Tyr L eu Thr Ser Glu Met Leu
            290                 295                 300

Ser Leu Ser Ala Ile Leu Ala Ile Thr Phe C ys Gly Ile Cys Cys Gln
305                 310                 315                 320

Lys Tyr Val Lys Ala Asn Ile Ser Glu Gln S er Ala Thr Thr Val Arg
                325                 330                 335

Tyr Thr Met Lys Met Leu Ala Ser Ser Ala G lu Thr Ile Ile Phe Met
            340                 345                 350

Phe Leu Gly Ile Ser Ala Val Asn Pro Phe I le Trp Thr Trp Asn Thr
            355                 360                 365

Ala Phe Val Leu Leu Thr Leu Val Phe Ile S er Val Tyr Arg Ala Ile
            370                 375                 380

Gly Val Val Leu Gln Thr Trp Leu Leu Asn A rg Tyr Arg Met Val Gln
385                 390                 395                 400

Leu Glu Pro Ile Asp Gln Val Val Leu Ser T yr Gly Gly Leu Arg Gly
                405                 410                 415

Ala Val Ala Phe Ala Leu Val Val Leu Leu A sp Gly Asp Lys Val Lys
                420                 425                 430

Glu Lys Asn Leu Phe Val Ser Thr Thr Ile I le Val Val Phe Phe Thr
            435                 440                 445

Val Ile Phe Gln Gly Leu Thr Ile Lys Pro L eu Val Gln Trp Leu Lys
            450                 455                 460

Val Lys Arg Ser Glu His Arg Glu Pro Arg L eu Asn Glu Lys Leu His
465                 470                 475                 480

Gly Arg Ala Phe Asp His Ile Leu Ser Ala I le Glu Asp Ile Ser Gly
                485                 490                 495
```

```
Gln Ile Gly His Asn Tyr Leu Arg Asp Lys Trp Ser His Phe Asp Arg
            500                 505                 510

Lys Phe Leu Ser Arg Val Leu Met Arg Arg Ser Ala Gln Lys Ser Arg
        515                 520                 525

Asp Arg Ile Leu Asn Val Phe His Glu Leu Asn Leu Lys Asp Ala Ile
        530                 535                 540

Ser Tyr Val Ala Glu Gly Glu Arg Gly Ser Leu Ala Phe Ile Arg
545                 550                 555                 560

Ser Pro Ser Thr Asp Asn Val Val Asn Val Asp Phe Thr Pro Arg Ser
            565                 570                 575

Ser Thr Val Glu Ala Ser Val Ser Tyr Leu Leu Arg Glu Asn Val Ser
        580                 585                 590

Ala Val Cys Leu Asp Met Gln Ser Leu Glu Gln Arg Arg Arg Ser Ile
        595                 600                 605

Arg Asp Ala Glu Asp Met Val Thr His His Thr Leu Gln Gln Tyr Leu
        610                 615                 620

Tyr Lys Pro Arg Gln Glu Tyr Lys His Leu Tyr Ser Arg His Glu Leu
625                 630                 635                 640

Thr Pro Thr Glu Asp Glu Lys Gln Asp Arg Glu Ile Phe His Arg Thr
            645                 650                 655

Met Arg Lys Arg Leu Glu Ser Phe Lys Ser Thr Lys Leu Gly Leu Asn
            660                 665                 670

Gln Asn Lys Lys Ala Ala Lys Leu Tyr Lys Arg Glu Arg Ala Gln Lys
        675                 680                 685

Arg Arg Asn Ser Ser Ile Pro Asn Gly Lys Leu Pro Met Glu Ser Pro
690                 695                 700

Ala Gln Asn Phe Thr Ile Lys Glu Lys Asp Leu Glu Leu Ser Asp Thr
705                 710                 715                 720

Glu Glu Pro Pro Asn Tyr Asp Glu Glu Met Ser Gly Gly Ile Glu Phe
            725                 730                 735

Leu Ala Ser Val Thr Lys Asp Thr Ala Ser Asp Ser Pro Ala Gly Ile
            740                 745                 750

Asp Asn Pro Val Phe Ser Pro Asp Glu Ala Leu Asp Arg Ser Leu Leu
        755                 760                 765

Ala Arg Leu Pro Pro Trp Leu Ser Pro Gly Glu Thr Val Val Pro Ser
770                 775                 780

Gln Arg Ala Arg Thr Gln Ile Pro Tyr Ser Pro Gly Thr Phe Arg Arg
785                 790                 795                 800

Leu Met Pro Phe Arg Leu Ser Ser Lys Ser Val Asp Ser Phe Leu Gln
            805                 810                 815

Ala Asp Gly Pro Glu Glu Arg Pro Pro Ala Ala Leu Pro Glu Ser Thr
            820                 825                 830

His Met
```

(2) INFORMATION FOR SEQ ID NO:10:

(i) SEQUENCE CHARACTERISTICS:
        (A) LENGTH: 834 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

-continued

```
Met Trp Gly Leu Gly Ala Arg Gly Pro Asp Arg Gly Leu Leu Ala
1               5                   10                  15

Leu Ala Leu Gly Gly Leu Ala Arg Ala Gly Gly Val Glu Val Glu Pro
            20                  25                  30

Gly Gly Ala His Gly Glu Ser Gly Gly Phe Gln Val Val Thr Phe Glu
                35                  40                  45

Trp Ala His Val Gln Asp Pro Tyr Val Ile Ala Leu Trp Ile Leu Val
50                      55                  60

Ala Ser Leu Ala Lys Ile Gly Phe His Leu Ser His Lys Val Thr Ser
65                  70                  75                  80

Val Val Pro Glu Ser Ala Leu Leu Ile Val Leu Gly Leu Val Leu Gly
                85                  90                  95

Gly Ile Val Trp Ala Ala Asp His Ile Ala Ser Phe Thr Leu Thr Pro
                100                 105                 110

Thr Val Phe Phe Phe Tyr Leu Leu Pro Pro Ile Val Leu Asp Ala Gly
            115                 120                 125

Tyr Phe Met Pro Asn Arg Leu Phe Phe Gly Asn Leu Gly Thr Ile Leu
            130                 135             140

Leu Tyr Ala Val Val Gly Thr Val Trp Asn Ala Ala Thr Thr Gly Leu
145                 150                 155                 160

Ser Leu Tyr Gly Val Phe Leu Ser Gly Leu Met Gly Asp Leu Gln Ile
                165                 170                 175

Gly Leu Leu Asp Phe Leu Leu Phe Gly Ser Leu Met Ala Ala Val Asp
            180                 185                 190

Pro Val Ala Val Leu Ala Val Phe Glu Glu Val His Val Asn Glu Val
            195                 200                 205

Leu Phe Ile Ile Val Phe Gly Glu Ser Leu Leu Asn Asp Ala Val Thr
210                 215                 220

Val Val Leu Tyr Asn Val Phe Glu Ser Phe Val Ala Leu Gly Gly Asp
225                 230                 235                 240

Asn Val Thr Gly Val Asp Cys Val Lys Gly Ile Val Ser Phe Phe Val
            245                 250                 255

Val Ser Leu Gly Gly Thr Leu Val Gly Val Val Phe Ala Phe Leu Leu
            260                 265                 270

Ser Leu Val Thr Arg Phe Thr Lys His Val Arg Ile Ile Glu Pro Gly
            275                 280                 285

Phe Val Phe Ile Ile Ser Tyr Leu Ser Tyr Leu Thr Ser Glu Met Leu
290                 295                 300

Ser Leu Ser Ala Ile Leu Ala Ile Thr Phe Cys Gly Ile Cys Cys Gln
305                 310                 315                 320

Lys Tyr Val Lys Ala Asn Ile Ser Glu Gln Ser Ala Thr Thr Val Arg
                325                 330                 335

Tyr Thr Met Lys Met Leu Ala Ser Ser Ala Glu Thr Ile Ile Phe Met
            340                 345                 350

Phe Leu Gly Ile Ser Ala Val Asn Pro Phe Ile Trp Thr Trp Asn Thr
            355                 360                 365

Ala Phe Val Leu Leu Thr Leu Val Phe Ile Ser Val Tyr Arg Ala Ile
370                 375                 380

Gly Val Val Leu Gln Thr Trp Leu Leu Asn Arg Tyr Arg Met Val Gln
385                 390                 395                 400

Leu Glu Pro Ile Asp Gln Val Val Leu Ser Tyr Gly Gly Leu Arg Gly
            405                 410                 415

Ala Val Ala Phe Ala Leu Val Val Leu Leu Asp Gly Asp Lys Val Lys
```

-continued

```
                420                 425                 430
Glu Lys Asn Leu Phe Val Ser Thr Thr Ile Ile Val Val Phe Phe Thr
                435                 440                 445
Val Ile Phe Gln Gly Leu Thr Ile Lys Pro Leu Val Gln Trp Leu Lys
450                 455                 460
Val Lys Arg Ser Glu His Arg Glu Pro Arg Leu Asn Glu Lys Leu His
465                 470                 475                 480
Gly Arg Ala Phe Asp His Ile Leu Ser Ala Ile Glu Asp Ile Ser Gly
                485                 490                 495
Gln Ile Gly His Asn Tyr Leu Arg Asp Lys Trp Ser His Phe Asp Arg
                500                 505                 510
Lys Phe Leu Ser Arg Val Leu Met Arg Arg Ser Ala Gln Lys Ser Arg
                515                 520                 525
Asp Arg Ile Leu Asn Val Phe His Glu Leu Asn Leu Lys Asp Ala Ile
                530                 535                 540
Ser Tyr Val Ala Glu Gly Glu Arg Arg Gly Ser Leu Ala Phe Ile Arg
545                 550                 555                 560
Ser Pro Ser Thr Asp Asn Val Val Asn Val Asp Phe Thr Pro Arg Ser
                565                 570                 575
Ser Thr Val Glu Ala Ser Val Ser Tyr Leu Leu Arg Glu Asn Val Ser
                580                 585                 590
Ala Val Cys Leu Asp Met Gln Ser Leu Glu Gln Arg Arg Arg Ser Ile
                595                 600                 605
Arg Asp Ala Glu Asp Met Val Thr His His Thr Leu Gln Gln Tyr Leu
                610                 615                 620
Tyr Lys Pro Arg Gln Glu Tyr Lys His Leu Tyr Ser Arg His Glu Leu
625                 630                 635                 640
Thr Pro Thr Glu Asp Glu Lys Gln Asp Arg Glu Ile Phe His Arg Thr
                645                 650                 655
Met Arg Lys Arg Leu Glu Ser Phe Lys Ser Thr Lys Leu Gly Leu Asn
                660                 665                 670
Gln Asn Lys Lys Ala Ala Lys Leu Tyr Lys Arg Glu Arg Ala Gln Lys
                675                 680                 685
Arg Arg Asn Ser Ser Ile Pro Asn Gly Lys Leu Pro Met Glu Ser Pro
690                 695                 700
Ala Gln Asn Phe Thr Ile Lys Glu Lys Asp Leu Glu Leu Ser Asp Thr
705                 710                 715                 720
Glu Glu Pro Pro Asn Tyr Asp Glu Glu Met Ser Gly Gly Ile Glu Phe
                725                 730                 735
Leu Ala Ser Val Thr Lys Asp Thr Ala Ser Asp Ser Pro Ala Gly Ile
                740                 745                 750
Asp Asn Pro Val Phe Ser Pro Asp Glu Ala Leu Asp Arg Ser Leu Leu
                755                 760                 765
Ala Arg Leu Pro Pro Trp Leu Ser Pro Gly Glu Thr Val Val Pro Ser
770                 775                 780
Gln Arg Ala Arg Thr Gln Ile Pro Tyr Ser Pro Gly Thr Phe Arg Arg
785                 790                 795                 800
Leu Met Pro Phe Arg Leu Ser Ser Lys Ser Val Asp Ser Phe Leu Gln
                805                 810                 815
Ala Asp Gly Pro Glu Glu Arg Pro Pro Ala Ala Leu Pro Glu Ser Thr
                820                 825                 830
His Met
```

(2) INFORMATION FOR SEQ ID NO:11:

(i) SEQUENCE CHARACTERISTICS:
        (A) LENGTH: 831 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Met Trp His Pro Ala Leu Gly Pro Gly Trp Lys Pro Leu Leu Ala Leu
  1               5                  10                  15

Ala Val Ala Val Thr Ser Leu Arg Gly Val Arg Gly Ile Glu Glu Glu
                 20                  25                  30

Pro Asn Ser Gly Gly Ser Phe Gln Ile Val Thr Phe Lys Trp His His
             35                  40                  45

Val Gln Asp Pro Tyr Ile Ile Ala Leu Trp Ile Leu Val Ala Ser Leu
         50                  55                  60

Ala Lys Ile Val Phe His Leu Ser His Lys Val Thr Ser Val Val Pro
 65                  70                  75                  80

Glu Ser Ala Leu Leu Ile Val Leu Gly Leu Val Leu Gly Gly Ile Val
                 85                  90                  95

Trp Ala Ala Asp His Ile Ala Ser Phe Thr Leu Thr Pro Thr Leu Phe
                100                 105                 110

Phe Phe Tyr Leu Leu Pro Pro Ile Val Leu Asp Ala Gly Tyr Phe Met
            115                 120                 125

Pro Asn Arg Leu Phe Phe Gly Asn Leu Gly Thr Ile Leu Leu Tyr Ala
        130                 135                 140

Val Ile Gly Thr Ile Trp Asn Ala Ala Thr Thr Gly Leu Ser Leu Tyr
145                 150                 155                 160

Gly Val Phe Leu Ser Gly Leu Met Gly Glu Leu Lys Ile Gly Leu Leu
                165                 170                 175

Asp Phe Leu Leu Phe Gly Ser Leu Ile Ala Ala Val Asp Pro Val Ala
            180                 185                 190

Val Leu Ala Val Phe Glu Glu Val His Val Asn Glu Val Leu Phe Ile
        195                 200                 205

Ile Val Phe Gly Glu Ser Leu Leu Asn Asp Ala Val Thr Val Val Leu
210                 215                 220

Tyr Asn Val Phe Glu Ser Phe Val Thr Leu Gly Gly Asp Ala Val Thr
225                 230                 235                 240

Gly Val Asp Cys Val Lys Gly Ile Val Ser Phe Phe Val Val Ser Leu
                245                 250                 255

Gly Gly Thr Leu Val Gly Val Ile Phe Ala Phe Leu Leu Ser Leu Val
            260                 265                 270

Thr Arg Phe Thr Lys His Val Arg Ile Ile Glu Pro Gly Phe Val Phe
        275                 280                 285

Val Ile Ser Tyr Leu Ser Tyr Leu Thr Ser Glu Met Leu Ser Leu Ser
        290                 295                 300

Ala Ile Leu Ala Ile Thr Phe Cys Gly Ile Cys Cys Gln Lys Tyr Val
305                 310                 315                 320

Lys Ala Asn Ile Ser Glu Gln Ser Ala Thr Thr Val Arg Tyr Thr Met
                325                 330                 335

Lys Met Leu Ala Ser Gly Ala Glu Thr Ile Ile Phe Met Phe Leu Gly
            340                 345                 350
```

-continued

```
Ile Ser Ala Val Asp Pro Val Ile Trp Thr Trp Asn Thr Ala Phe Val
        355                 360                 365

Leu Leu Thr Leu Val Phe Ile Ser Val Tyr Arg Ala Ile Gly Val Val
        370                 375                 380

Leu Gln Thr Trp Ile Leu Asn Arg Tyr Arg Met Val Gln Leu Glu Thr
385                 390                 395                 400

Ile Asp Gln Val Val Met Ser Tyr Gly Gly Leu Arg Gly Ala Val Ala
                405                 410                 415

Tyr Ala Leu Val Val Leu Leu Asp Glu Lys Lys Val Lys Glu Lys Asn
                420                 425                 430

Leu Phe Val Ser Thr Thr Leu Ile Val Val Phe Phe Thr Val Ile Phe
        435                 440                 445

Gln Gly Leu Thr Ile Lys Pro Leu Val Gln Trp Leu Lys Val Lys Arg
450                 455                 460

Ser Glu Gln Arg Glu Pro Lys Leu Asn Glu Lys Leu His Gly Arg Ala
465                 470                 475                 480

Phe Asp His Ile Leu Ser Ala Ile Glu Asp Ile Ser Gly Gln Ile Gly
                485                 490                 495

His Asn Tyr Leu Arg Asp Lys Trp Ser Asn Phe Asp Arg Lys Phe Leu
                500                 505                 510

Ser Lys Val Leu Met Arg Arg Ser Ala Gln Lys Ser Arg Asp Arg Ile
        515                 520                 525

Leu Asn Val Phe His Glu Leu Asn Leu Lys Asp Ala Ile Ser Tyr Val
        530                 535                 540

Ala Glu Gly Glu Arg Arg Gly Ser Leu Ala Phe Ile Arg Ser Pro Ser
545                 550                 555                 560

Thr Asp Asn Met Val Asn Val Asp Phe Ser Thr Pro Arg Pro Ser Thr
                565                 570                 575

Val Glu Ala Ser Val Ser Tyr Phe Leu Arg Glu Asn Val Ser Ala Val
                580                 585                 590

Cys Leu Asp Met Gln Ser Leu Glu Gln Arg Arg Arg Ser Ile Arg Asp
        595                 600                 605

Thr Glu Asp Met Val Thr His His Thr Leu Gln Gln Tyr Leu Tyr Lys
        610                 615                 620

Pro Arg Gln Glu Tyr Lys His Leu Tyr Ser Arg His Glu Leu Thr Pro
625                 630                 635                 640

Asn Glu Asp Glu Lys Gln Asp Lys Glu Ile Phe His Arg Thr Met Arg
                645                 650                 655

Lys Arg Leu Glu Ser Phe Lys Ser Ala Lys Leu Gly Ile Asn Gln Asn
                660                 665                 670

Lys Lys Ala Ala Lys Leu Tyr Lys Arg Glu Arg Ala Gln Lys Arg Arg
        675                 680                 685

Asn Ser Ser Ile Pro Asn Gly Lys Leu Pro Met Glu Asn Leu Ala His
690                 695                 700

Asn Phe Thr Ile Lys Glu Lys Asp Leu Glu Leu Ser Glu Pro Glu Glu
705                 710                 715                 720

Ala Thr Asn Tyr Glu Glu Ile Ser Gly Gly Ile Glu Phe Leu Ala Ser
                725                 730                 735

Val Thr Lys Asp Val Ala Ser Asp Ser Gly Ala Gly Ile Asp Asn Pro
                740                 745                 750

Val Phe Ser Pro Asp Glu Asp Leu Asp Pro Ser Ile Leu Ser Arg Val
        755                 760                 765

Pro Pro Trp Leu Ser Pro Gly Glu Thr Val Val Pro Ser Gln Arg Ala
```

-continued

```
            770                 775                 780
Arg Val Gln Ile Pro Asn Ser Pro Ser Asn Phe Arg Arg Leu Thr Pro
785                 790                 795                 800

Phe Arg Leu Ser Asn Lys Ser Val Asp Ser Phe Leu Gln Ala Asp Gly
                805                 810                 815

Pro Glu Glu Gln Leu Gln Pro Ala Ser Pro Glu Ser Thr His Met
                820                 825                 830
```

(2) INFORMATION FOR SEQ ID NO:12:

(i) SEQUENCE CHARACTERISTICS:
       (A) LENGTH: 832 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:12:

```
Met Ser Gly Arg Gly Gly Cys Gly Pro Cys Trp Gly Leu Leu Leu Ala
1               5                   10                  15

Leu Val Leu Ala Leu Gly Ala Leu Pro Trp Thr Gln Gly Ala Glu Gln
                20                  25                  30

Glu His His Asp Glu Ile Gln Gly Phe Gln Ile Val Thr Phe Lys Trp
                35                  40                  45

His His Val Gln Asp Pro Tyr Ile Ile Ala Leu Trp Val Leu Val Ala
                50                  55                  60

Ser Leu Ala Lys Ile Val Phe His Leu Ser His Lys Val Thr Ser Val
65                  70                  75                  80

Val Pro Glu Ser Ala Leu Leu Ile Val Leu Gly Leu Val Leu Gly Gly
                85                  90                  95

Ile Val Leu Ala Ala Asp His Ile Ala Ser Phe Thr Leu Thr Pro Thr
                100                 105                 110

Val Phe Phe Phe Tyr Leu Leu Pro Pro Ile Val Leu Asp Ala Gly Tyr
                115                 120                 125

Phe Met Pro Asn Arg Leu Phe Phe Ser Asn Leu Gly Ser Ile Leu Leu
                130                 135                 140

Tyr Ala Val Val Gly Thr Val Trp Asn Ala Ala Thr Thr Gly Leu Ser
145                 150                 155                 160

Leu Tyr Gly Val Phe Leu Ser Gly Ile Met Gly Glu Leu Lys Ile Gly
                165                 170                 175

Leu Leu Asp Phe Leu Leu Phe Gly Ser Leu Ile Ala Ala Val Asp Pro
                180                 185                 190

Val Ala Val Leu Ala Val Phe Glu Glu Val His Val Asn Glu Val Leu
                195                 200                 205

Phe Ile Ile Val Phe Gly Glu Ser Leu Leu Asn Asp Ala Val Thr Val
                210                 215                 220

Val Leu Tyr Asn Val Phe Gln Ser Phe Val Thr Leu Gly Gly Asp Lys
225                 230                 235                 240

Val Thr Gly Val Asp Cys Val Lys Gly Ile Val Ser Phe Phe Val Val
                245                 250                 255

Ser Leu Gly Gly Thr Leu Val Gly Val Val Phe Ala Phe Leu Leu Ser
                260                 265                 270

Leu Val Thr Arg Phe Thr Lys His Val Arg Val Ile Glu Pro Gly Phe
                275                 280                 285

Val Phe Ile Ile Ser Tyr Leu Ser Tyr Leu Thr Ser Glu Met Leu Ser
```

-continued

```
            290                 295                 300
Leu Ser Ser Ile Leu Ala Ile Thr Phe Cys Gly Ile Cys Cys Gln Lys
305                 310                 315                 320

Tyr Val Lys Ala Asn Ile Ser Glu Gln Ser Ala Thr Thr Val Arg Tyr
                325                 330                 335

Thr Met Lys Met Leu Ala Ser Gly Ala Glu Thr Ile Ile Phe Met Phe
                340                 345                 350

Leu Gly Ile Ser Ala Val Asp Pro Leu Ile Trp Thr Trp Asn Thr Ala
                355                 360                 365

Phe Val Arg Leu Thr Leu Leu Phe Val Ser Val Phe Arg Ala Ile Gly
370                 375                 380

Val Val Leu Gln Thr Trp Leu Leu Asn Arg Tyr Arg Met Val Gln Leu
385                 390                 395                 400

Glu Leu Ile Asp Gln Val Val Met Ser Tyr Gly Gly Leu Arg Gly Ala
                405                 410                 415

Val Ala Phe Ala Leu Val Ala Leu Leu Asp Gly Asn Lys Val Lys Glu
                420                 425                 430

Lys Asn Leu Phe Val Ser Thr Thr Ile Ile Val Val Phe Phe Thr Val
                435                 440                 445

Ile Phe Gln Gly Leu Thr Ile Lys Pro Leu Val Gln Trp Leu Lys Val
450                 455                 460

Lys Arg Ser Glu His Arg Glu Pro Lys Leu Asn Glu Lys Leu His Gly
465                 470                 475                 480

Arg Ala Phe Asp His Ile Leu Ser Ala Ile Glu Asp Ile Ser Gly Gln
                485                 490                 495

Ile Gly His Asn Tyr Leu Arg Asp Lys Trp Ala Asn Phe Asp Arg Arg
                500                 505                 510

Phe Leu Ser Lys Leu Leu Met Arg Gln Ser Ala Gln Lys Ser Arg Asp
                515                 520                 525

Arg Ile Leu Asn Val Phe His Glu Leu Asn Leu Lys Asp Ala Ile Ser
                530                 535                 540

Tyr Val Thr Glu Gly Glu Arg Arg Gly Ser Leu Ala Phe Ile Arg Ser
545                 550                 555                 560

Pro Ser Thr Asp Asn Met Val Asn Val Asp Phe Ser Thr Pro Arg Pro
                565                 570                 575

Ser Thr Val Glu Ala Ser Val Ser Tyr Leu Leu Arg Glu Ser Ala Ser
                580                 585                 590

Ala Val Cys Leu Asp Met Gln Ser Leu Glu Gln Arg Arg Arg Ser Val
                595                 600                 605

Arg Asp Ala Glu Asp Val Ile Thr His His Thr Leu Gln Gln Tyr Leu
                610                 615                 620

Tyr Lys Pro Arg Gln Glu Tyr Lys His Leu Tyr Ser Arg His Val Leu
625                 630                 635                 640

Ser Pro Ser Glu Asp Glu Lys Gln Asp Lys Glu Ile Phe His Arg Thr
                645                 650                 655

Met Arg Lys Arg Leu Glu Ser Phe Lys Ser Ala Lys Leu Gly Leu Gly
                660                 665                 670

Gln Ser Lys Lys Ala Thr Lys His Lys Arg Glu Arg Glu Arg Ala Gln
                675                 680                 685

Lys Arg Arg Asn Ser Ser Val Pro Asn Gly Lys Leu Pro Leu Asp Ser
                690                 695                 700

Pro Arg Tyr Gly Leu Thr Leu Lys Glu Arg Glu Leu Glu Leu Ser Asp
705                 710                 715                 720
```

-continued

```
Pro Glu Glu Ala Pro Asp Tyr Tyr Glu Ala G lu Lys Met Ser Gly Gly
            725                 730                735

Ile Glu Phe Leu Ala Ser Val Thr Lys Val S er Thr Ser Asp Ser Pro
            740                 745                750

Ala Gly Ile Asp Asn Pro Val Phe Ser Pro A sp Glu Asp Leu Ala Pro
            755             760             765

Ser Leu Leu Ala Arg Val Pro Pro Trp Leu S er Pro Gly Glu Ala Val
    770             775                 780

Val Pro Ser Gln Arg Ala Arg Val Gln Ile P ro Tyr Ser Pro Gly Asn
785             790             795                     800

Phe Arg Arg Leu Ala Pro Phe Arg Leu Ser A sn Lys Ser Val Asp Ser
                805             810                 815

Phe Leu Leu Ala Glu Asp Gly Ala Glu His P ro Glu Ser Thr His Met
                820             825             830
```

We claim:

1. A human $Na^+/H^+$ exchanger protein with the sequence of SEQ ID NO:9, or a functional portion thereof, isolated from other human proteins.

2. A protein in accordance with claim 1 it whose sequence is that of SEQ ID NO:9.

3. A non-human cell having expressed thereon a human $Na^+/H^+$ exchanger protein with the sequence of SEQ ID NO:9, or a functional portion thereof.

4. A non-human cell in accordance with claim 3, which, aside from the human $Na^+/H^+$ protein or functional portion thereof which is expressed thereon, is deficient of $Na^+H^+$ exchange proteins.

5. A non-human cell in accordance with claim 3, having expressed thereon a human $Na^+/H^+$ exchanger protein with the sequence of SEQ ID NO:9.

6. A non-human cell in accordance with claim 5, which, aside from the human $Na^+/H^+$ protein which is expressed thereon, is deficient of $Na^+/H^+$ exchange proteins.

7. A non-human cell having expressed thereon a human $Na^+/H^+$ exchanger protein with the sequence of SEQ:ID NO:9, or a functional portion thereof, said cell comprising DNA encoding said protein or functional portion thereof.

* * * * *